(12) United States Patent
Braun

(10) Patent No.: US 12,232,781 B2
(45) Date of Patent: Feb. 25, 2025

(54) CORTICAL/CANCELLOUS BONE PROBES AND RELATED SURGICAL METHODS

(71) Applicant: BaunVest, LLC, Charlotte, VT (US)

(72) Inventor: John T. Braun, Charlotte, VT (US)

(73) Assignee: BraunVest, LLC, Charlotte, VT (US)

(*) Notice: Subject to any disclaimer, the term of this patent is extended or adjusted under 35 U.S.C. 154(b) by 1049 days.

(21) Appl. No.: 17/063,674

(22) Filed: Oct. 5, 2020

(65) Prior Publication Data

US 2021/0045784 A1 Feb. 18, 2021

Related U.S. Application Data

(63) Continuation-in-part of application No. 16/526,664, filed on Jul. 30, 2019, now Pat. No. 11,648,000.

(60) Provisional application No. 62/910,333, filed on Oct. 3, 2019, provisional application No. 62/712,158, filed on Jul. 30, 2018.

(51) Int. Cl.
  *A61B 17/16* (2006.01)
  *A61B 17/70* (2006.01)
  *A61B 90/00* (2016.01)
  *A61B 17/00* (2006.01)

(52) U.S. Cl.
  CPC .......... *A61B 17/7076* (2013.01); *A61B 90/39* (2016.02); *A61B 2017/00075* (2013.01); *A61B 2017/00115* (2013.01); *A61B 2017/00367* (2013.01); *A61B 2090/3966* (2016.02)

(58) Field of Classification Search
  CPC ............ A61B 17/1604; A61B 17/1655; G01R 1/06722
  See application file for complete search history.

(56) References Cited

U.S. PATENT DOCUMENTS 3,562,643 A * 2/1971 Smith ................ G01R 1/06722
  324/72.5
4,783,624 A * 11/1988 Sabin ................ G01R 1/07314
  324/755.05

(Continued)

FOREIGN PATENT DOCUMENTS

WO   WO2009128074   10/2009
WO   WO2017127532   7/2017
WO   WO-2018050768 A1 * 3/2018

OTHER PUBLICATIONS

USPTO Non-Final Rejection, U.S. Appl. No. 16/526,664, dated Aug. 22, 2022 (15 pgs).

(Continued)

*Primary Examiner* — Zade Coley
(74) *Attorney, Agent, or Firm* — Matthew D. Thayne; Thayne and Davis LLC

(57) ABSTRACT

Vertebral probes for spinal surgeries and related surgical methods. In some embodiments, the probe may comprise a bicortical, vertebral probe that may comprise a shaft and a distal tip configured to penetrate a vertebral body to facilitate subsequent placement of a bone anchor providing bicortical purchase within the vertebral body. One or more features for facilitating safe placement of the probe may be provided, such as making the tip spring-loaded or otherwise axially movable relative to the shaft, providing sensors, and/or providing means for determining a position of the tip within a vertebral body.

19 Claims, 18 Drawing Sheets

(56) References Cited

U.S. PATENT DOCUMENTS

| | | | |
|---|---|---|---|
| 5,318,570 A * | 6/1994 | Hood | A61B 17/8847 601/2 |
| 5,387,213 A | 2/1995 | Breard et al. | |
| 5,827,290 A * | 10/1998 | Bradley | A61B 17/1604 606/85 |
| 5,951,560 A | 9/1999 | Simon et al. | |
| 6,080,173 A * | 6/2000 | Williamson, IV | A61B 17/32053 606/184 |
| 6,299,613 B1 | 10/2001 | Ogilvie et al. | |
| 6,677,772 B1 * | 1/2004 | Faull | G01R 1/06722 324/755.05 |
| 7,285,121 B2 | 10/2007 | Braun et al. | |
| 7,297,146 B2 | 11/2007 | Braun et al. | |
| 7,580,743 B2 | 8/2009 | Bourlion et al. | |
| 7,637,978 B2 | 12/2009 | Jung | |
| 7,691,131 B2 | 4/2010 | Graf | |
| 7,727,258 B2 | 6/2010 | Graf | |
| 7,845,945 B2 | 12/2010 | Canter | |
| 8,172,880 B2 | 5/2012 | Graf | |
| 8,177,810 B2 | 5/2012 | Ferree | |
| 8,221,457 B2 | 7/2012 | Delecrin et al. | |
| 8,419,476 B1 | 4/2013 | Bourlion et al. | |
| 8,486,119 B2 | 7/2013 | Bourlion | |
| 8,641,736 B2 | 2/2014 | Marik et al. | |
| 8,979,874 B2 | 3/2015 | Darois et al. | |
| 9,433,442 B2 | 9/2016 | Lindemann et al. | |
| 9,833,230 B2 | 12/2017 | Stone | |
| 10,179,015 B2 | 1/2019 | Lavigne et al. | |
| 2002/0032447 A1 * | 3/2002 | Weikel | A61B 17/7061 606/86 R |
| 2002/0055783 A1 * | 5/2002 | Tallarida | A61B 17/1764 623/20.14 |
| 2002/0077641 A1 * | 6/2002 | Michelson | A61B 17/025 606/167 |
| 2002/0082598 A1 | 6/2002 | Teitelbaum | |
| 2002/0143343 A1 * | 10/2002 | Castro | A61B 17/1757 606/90 |
| 2002/0173794 A1 * | 11/2002 | Happonen | A61B 17/1655 606/79 |
| 2003/0018337 A1 * | 1/2003 | Davis | A61B 17/1655 606/80 |
| 2003/0036764 A1 * | 2/2003 | Hamada | A61F 2/4601 606/102 |
| 2003/0109883 A1 * | 6/2003 | Matsuzaki | A61B 17/1671 606/86 R |
| 2005/0043738 A1 * | 2/2005 | Ryan | A61B 17/1604 606/80 |
| 2005/0070907 A1 * | 3/2005 | Abernathie | A61B 17/1655 606/80 |
| 2005/0171551 A1 * | 8/2005 | Sukovich | A61B 17/0218 606/86 R |
| 2006/0235306 A1 * | 10/2006 | Cotter | A61B 17/1688 600/459 |
| 2007/0219554 A1 * | 9/2007 | Landry | A61B 17/7035 623/17.16 |
| 2009/0312782 A1 * | 12/2009 | Park | A61F 2/0811 606/184 |
| 2010/0131010 A1 | 5/2010 | Graf | |
| 2010/0249497 A1 | 9/2010 | Peine et al. | |
| 2011/0054537 A1 * | 3/2011 | Miller | A61B 17/88 606/279 |
| 2011/0238069 A1 * | 9/2011 | Zajac | A61B 17/1655 606/79 |
| 2012/0189984 A1 | 7/2012 | Holmes | |
| 2013/0253587 A1 | 9/2013 | Carls et al. | |
| 2016/0374661 A1 * | 12/2016 | Housman | A61B 17/0401 606/232 |
| 2020/0155728 A1 * | 5/2020 | Brunelle | A61B 17/32 |
| 2021/0293852 A1 * | 9/2021 | König | G01R 1/06722 |

OTHER PUBLICATIONS

AccuSpine, Johns Hopkins University, https://www.invent.org/sites/default/files/2018-10/AccuSpine_Essay.pdf, dated Oct. 2018 (7 pgs).

USPTO Final Rejection, U.S. Appl. No. 16/526,664, dated Mar. 9, 2022 (12 pgs).

USPTO Non-Final Rejection, U.S. Appl. No. 16/526,664, dated Nov. 24, 2021 (9 pgs).

* cited by examiner

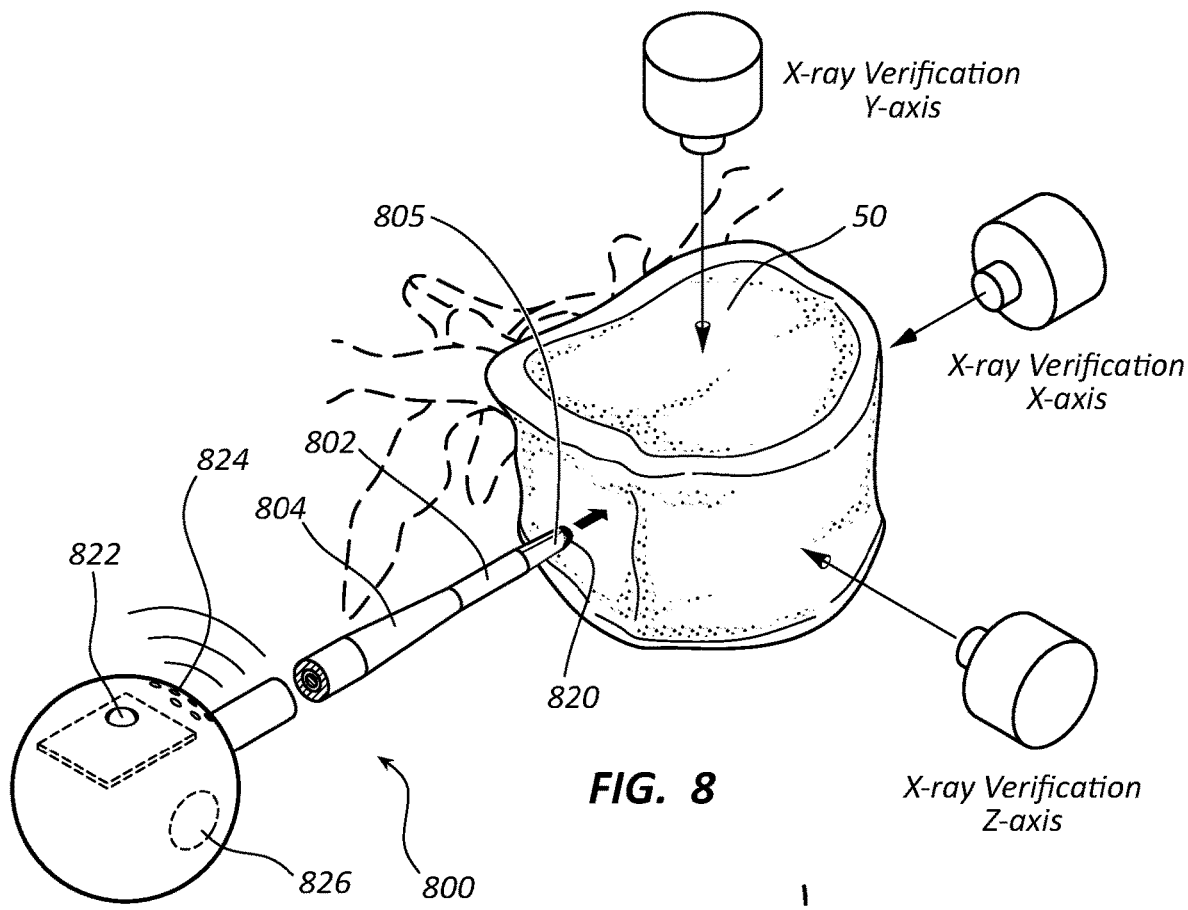
FIG. 8
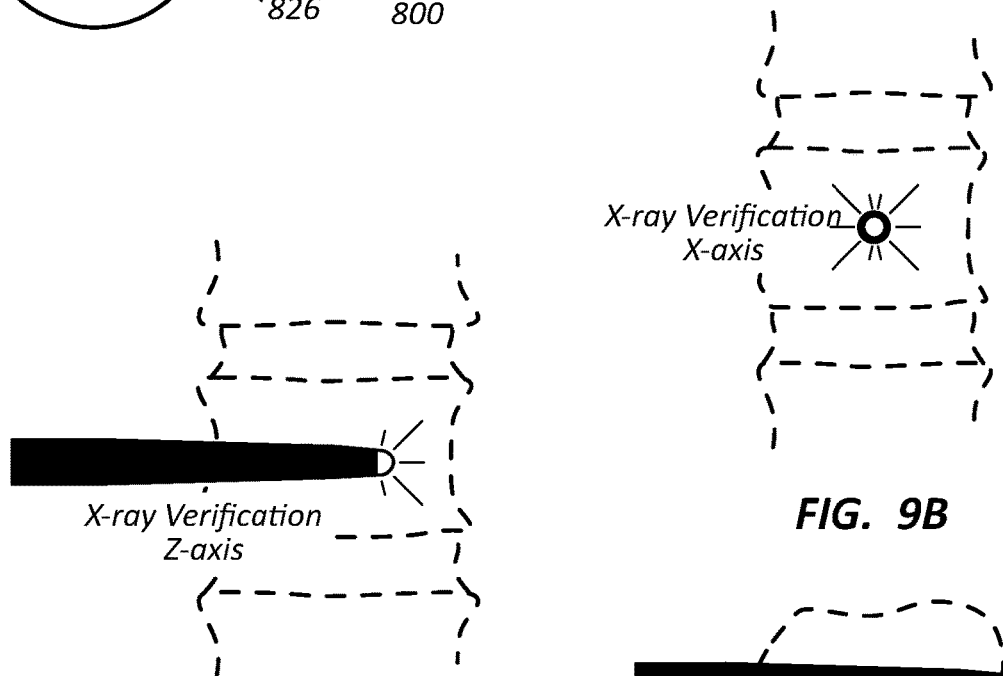
FIG. 9A
FIG. 9B
FIG. 9C

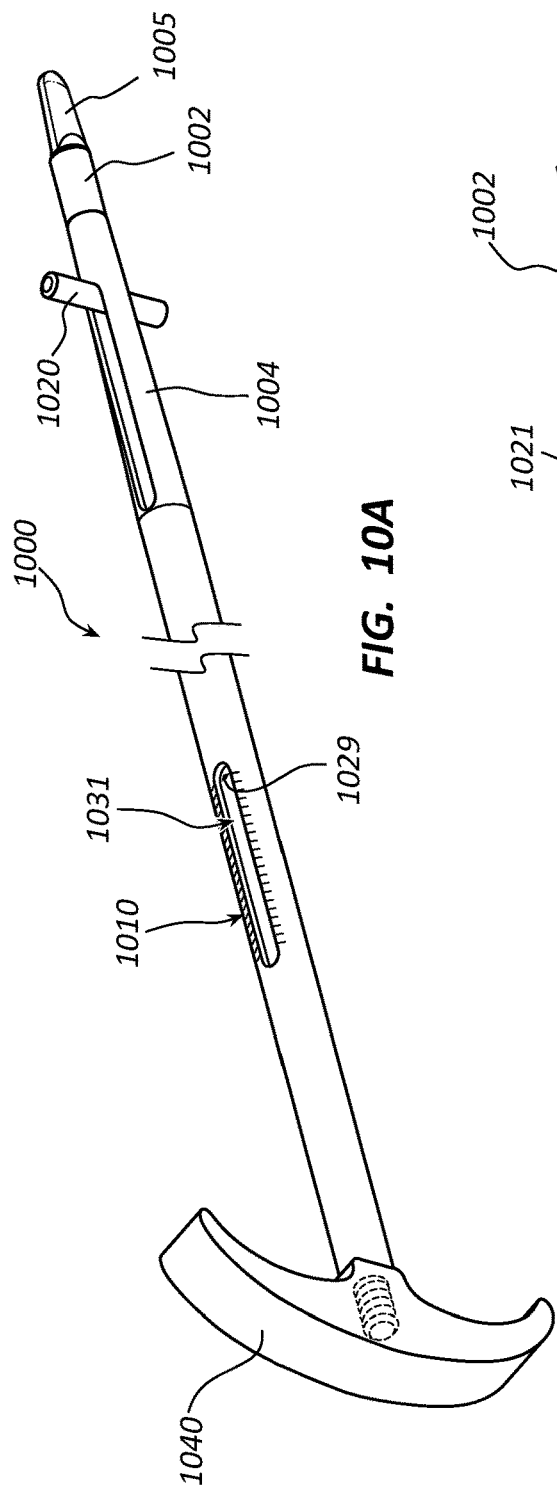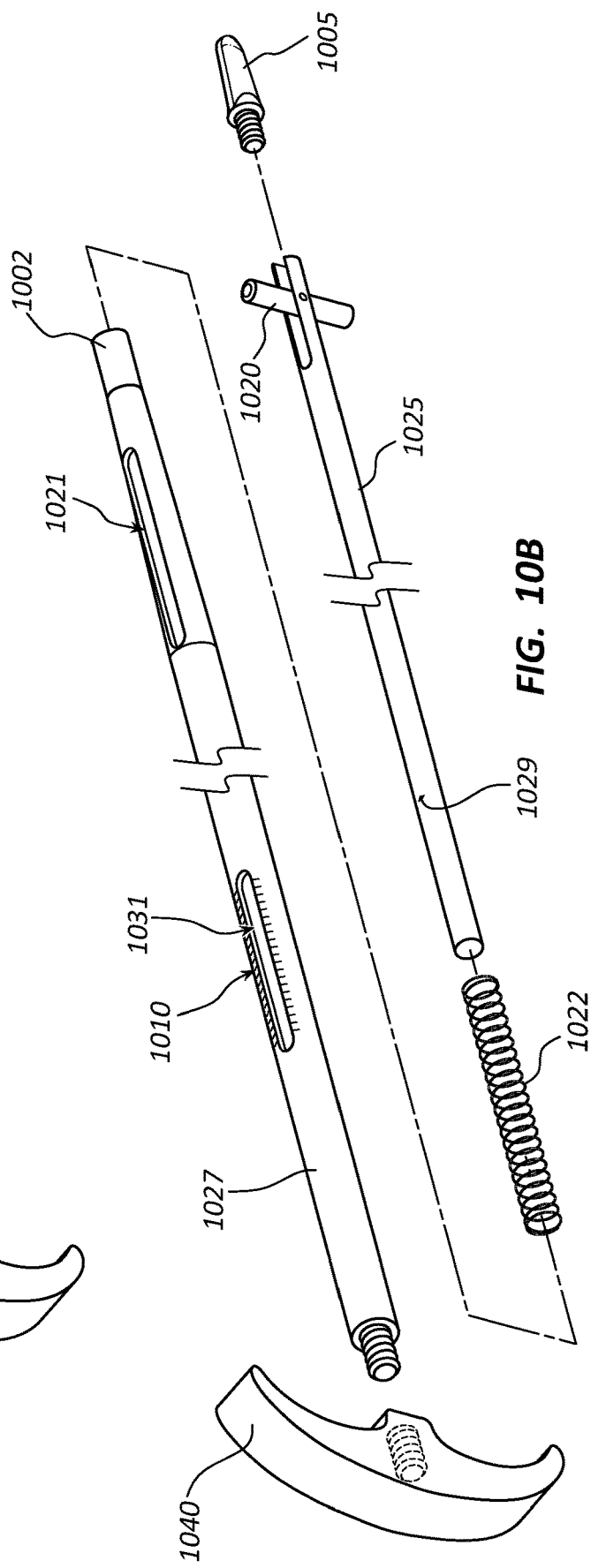
FIG. 10A
FIG. 10B

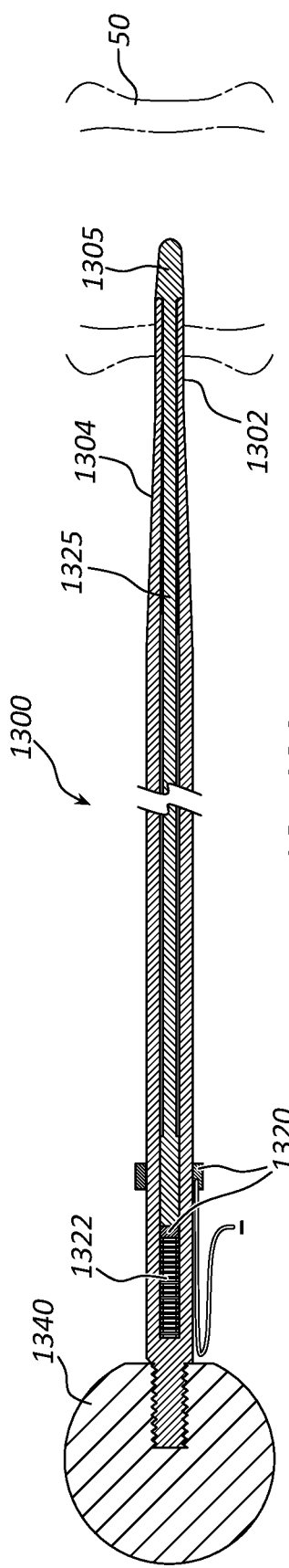
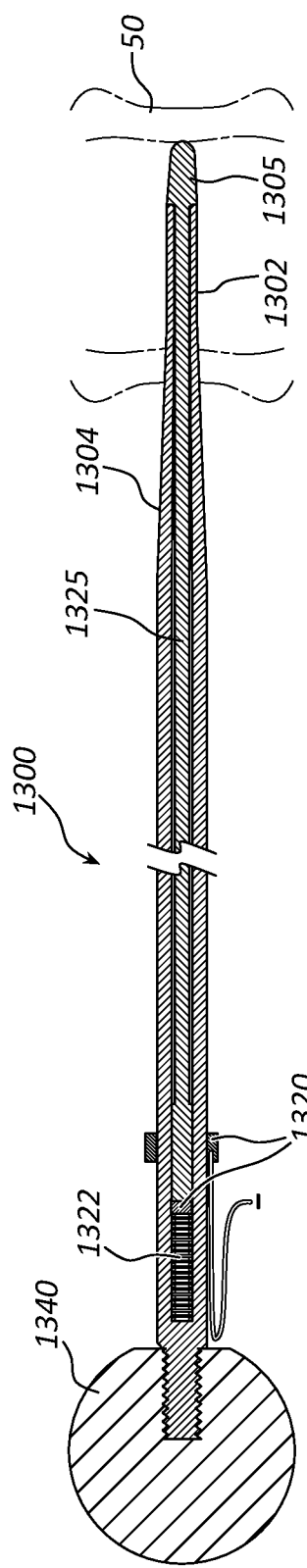
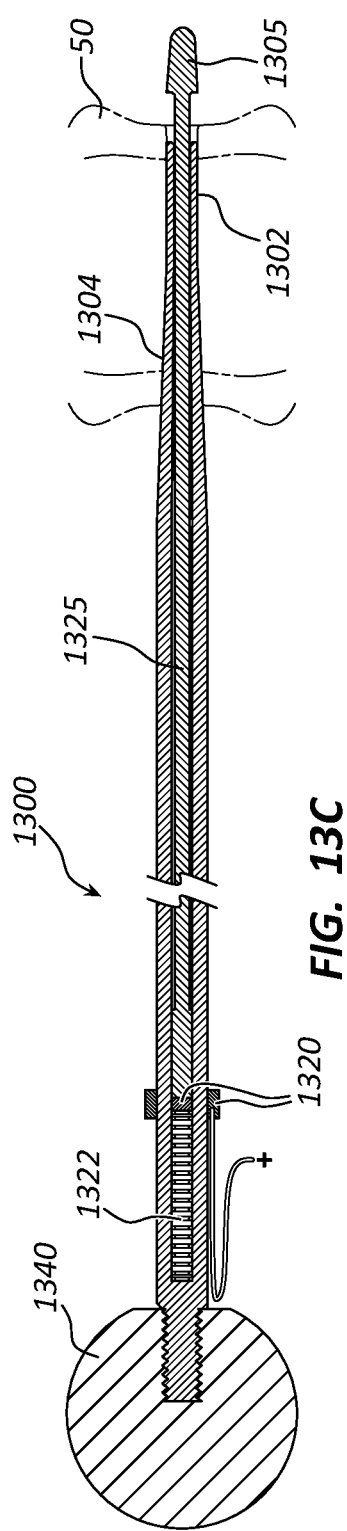
FIG. 13A
FIG. 13B
FIG. 13C

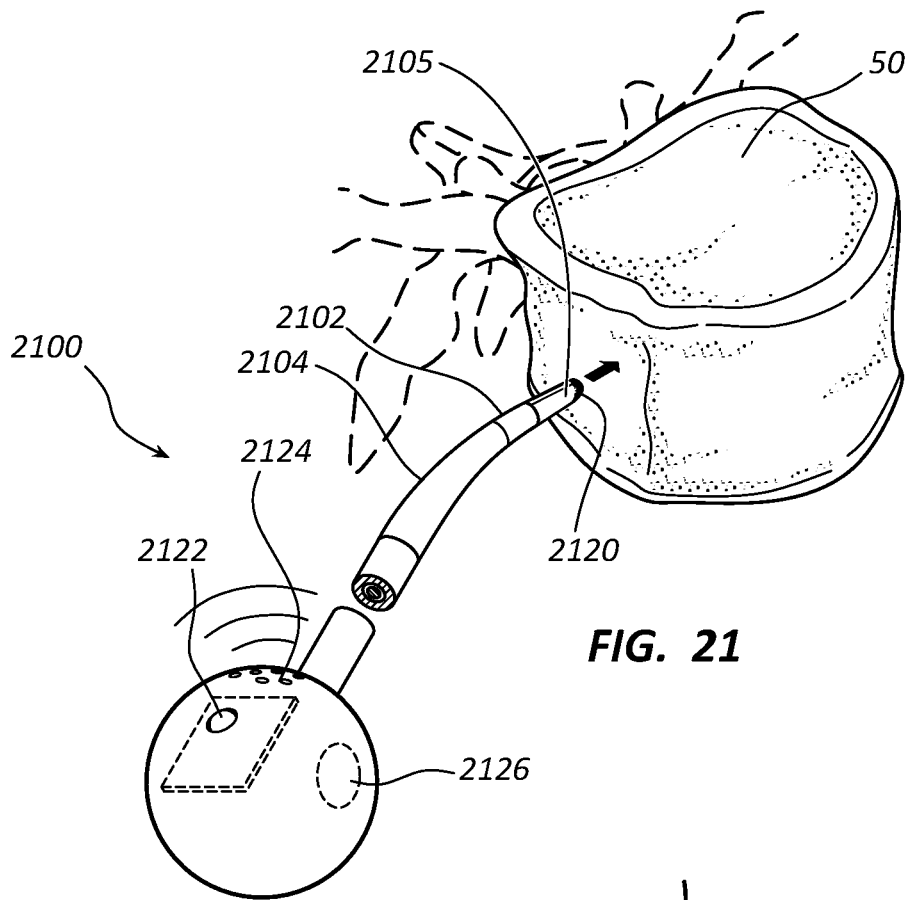
FIG. 21
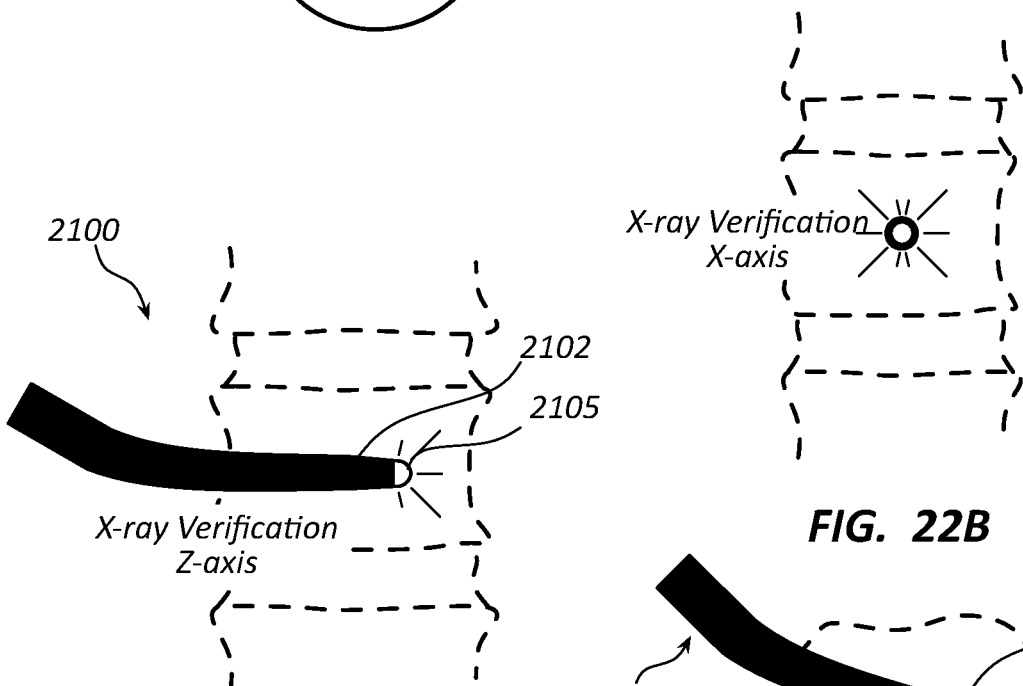
FIG. 22A
FIG. 22B
FIG. 22C

CORTICAL/CANCELLOUS BONE PROBES AND RELATED SURGICAL METHODS

CROSS-REFERENCE TO RELATED APPLICATIONS

This application claims the benefit under 35 U.S.C. § 119(e) of U.S. Provisional Patent Application No. 62/910,333, which was filed on Oct. 3, 2019 and is titled "CORTICAL/CANCELLOUS BONE PROBES AND RELATED SURGICAL METHODS." This application is also a continuation-in-part of U.S. patent application Ser. No. 16/526,664, which was filed on Jul. 30, 2019 and is titled "VERTEBRAL PROBES AND RELATED SURGICAL METHODS," which claims the benefit under 35 U.S.C. § 119(e) of U.S. Provisional Patent Application No. 62/712,158, which was filed Jul. 30, 2018 and is also titled "VERTEBRAL PROBES AND RELATED SURGICAL METHODS." Each of the aforementioned patent applications is hereby incorporated herein by reference in their entireties.

SUMMARY

Embodiments of apparatus and methods are disclosed herein that relate to bone probes. In some specific embodiments disclosed herein, such probes may comprise vertebral probes that may be used in certain spinal surgeries, particularly fusionless spinal surgeries, such as scoliosis surgeries.

Surgeons often use pedicle probes as vertebral probes to prepare for placement of bone screws in a patient's vertebral column. However, such probes are not designed for use in vertebral bodies and suffer from several drawbacks that make them less than ideal for this use. For example, such probes typically lack any features that allow a surgeon to feel or otherwise readily determine the placement of the probe within the vertebral body, that inhibit the probe from being advanced too far through a vertebral body, and/or that allow a surgeon to very precisely select an appropriate screw length for subsequent fixation to the vertebrae.

The present inventor has therefore determined that it would be desirable to provide systems and methods that overcome one or more of the foregoing limitations and/or other limitations of the prior art. Thus, in a more specific example of a vertebral probe, the probe may comprise a shaft having one or more tapering portions. Some embodiments may further comprise one or more non-tapering portions. The probe may comprise a distal tip extending from a shelf or ledge that may allow for penetration of the tip therethrough with a first force and be configured to inhibit further advancement of the probe by requiring a second force substantially greater than the first force to achieve further advancement.

In some embodiments, the probe may comprise one or more sections having a circular cross-section and the tip may comprise a non-circular cross-section, in whole or in part, such as flattened upper and/or lower surfaces forming a "duckbill" shape extending from a distal end of the probe.

Some embodiments may further comprise various other features, such as sections having distinct markings to indicate generally a current position of the probe within a vertebral body. Such markings may vary section by section to provide an easy way of visualizing advancement of the probe at one or more critical steps during a probing procedure. More precise markings may be provided to allow a surgeon to select a specific bone screw or other anchor for subsequent fixation to the vertebrae.

In a specific example of a vertebral probe for use in spinal surgeries, the probe may comprise a shaft having a circular cross section at least in part and a tip positioned at a distal end of the shaft and configured to penetrate a vertebral body to facilitate subsequent placement of a bone anchor providing bicortical purchase within the vertebral body. The tip may comprise a non-circular shape in cross-section at least in part.

In some embodiments, the shaft may comprise a tapering portion and a non-tapering portion. In some such embodiments, the non-tapering portion may be positioned adjacent to the tip. In some embodiments, the shaft may further comprise a second non-tapering portion, wherein the tapering portion is positioned in between the non-tapering portion and the second non-tapering portion.

In some embodiments, the tip may be defined, at least in part, by opposing flat surfaces extending from the shaft. The shaft may further comprise one or more shelves that may extend at an angle (in some embodiments a perpendicular or at least substantially perpendicular angle) relative to at least one of the opposing flat surfaces of the tip. In some such embodiments, the shaft may comprise two opposing shelves extending an angle relative to each of the two opposing flat surfaces of the tip.

In some embodiments, the vertebral probe may be configured to allow for penetration of the tip through a cortical wall of a vertebral body with a first force and further configured to inhibit further advancement of the vertebral probe by requiring a second force substantially greater than the first force to achieve further advancement of the vertebral probe within the vertebral body.

In some embodiments, the shaft may comprise a plurality of markings configured to allow a user to identify a current position of the vertebral probe within a vertebral body. In some such embodiments, the plurality of markings may comprise a plurality of marking sections, wherein each marking section is visually distinguishable from an adjacent marking section other than with distinct alphanumeric characters such that the plurality of marking sections is configured to provide a user with an indication of an extent to which the vertebral probe has penetrated a vertebral body without use of alphanumeric characters.

In another example of a vertebral probe according to some embodiments, the probe may comprise a shaft comprising at least one tapering portion and at least one non-tapering portion and a tip positioned at a distal end of the shaft and configured to penetrate a vertebral body to facilitate subsequent placement of a bone anchor providing bicortical purchase within the vertebral body. The tip may be set apart from the shaft at a shelf defining an engaging surface for increasing an insertion force of the vertebral probe during advancement through a vertebral body. The tip may be lacking in any sharp points.

In some embodiments, the tip may comprise a non-circular shape in cross section.

In some embodiments, the shelf may extend about an entire periphery of the tip.

Some embodiments may further comprise a second shelf defining a second engaging surface for increasing an insertion force of the vertebral probe during advancement through a vertebral body.

In some embodiments, the tip may be defined, at least in part, by opposing flat surfaces extending from the shaft. In some such embodiments, the tip may be further defined by opposing tapered edges extending to a rounded and blunt tip.

In an example of a method for preparing a vertebral body for receipt of a bicortical bone anchor according to some implementations, the method may comprise advancing a tip of a vertebral probe through a proximal cortical wall of a vertebral body. The vertebral probe may comprise a shelf defining a boundary between a shaft of the vertebral probe and the tip. The method may further comprise engaging the shelf with an outer surface of the proximal cortical wall to inhibit further advancement of the tip.

Some implementations may further comprise rotating the vertebral probe to form a chamber, such as a chamber having a circular cross section, within the vertebral body adjacent to the proximal cortical wall.

Some implementations may further comprise, following the step of rotating the vertebral probe, advancing the vertebral probe through the vertebral body such that the tip contacts and penetrates the distal cortical wall of the vertebral body and engaging the shelf with an inner surface of the distal cortical wall to inhibit further advancement of the tip.

In some implementations, following the step of engaging the shelf with an inner surface of the distal cortical wall, the vertebral probe may be rotated again to form a circular opening at the distal cortical wall.

In another example of a vertebral probe according to some embodiments, the probe may comprise a spring-loaded or otherwise biased tip. In some such embodiments, the tip may be biased distally such that, as the tip is being advanced through a vertebral body, it compresses and then, following breach of the distal cortical wall, the tip automatically advances a predetermined amount. In other embodiments, the tip may be biased in the proximal direction. In such embodiments, the tip may be advanced relative to one or more other portions of the probe by a predetermined distance by punching the tip forward through the distal cortical wall by the predetermined distance after the tip has contacted the distal cortical wall. The tip may also comprise other features described herein such as, for example, being set apart from the shaft at a shelf defining an engaging surface for increasing an insertion force of the vertebral probe during advancement through a vertebral body.

In another example of a vertebral probe according to still other embodiments, the probe may comprise sensors and/or other features to provide a visual and/or audible indication of a depth of the probe. For example, a member may be provided that is slidable or otherwise movable relative to one or more other portions of the probe that may be used, along with markings, to provide an indication of this depth. In some such embodiments, the member may be configured to engage a proximal cortical wall or other entry site within a bone and/or may be spring-loaded or otherwise biased to maintain contact with such bone during probing. This member may comprise, for example, a sleeve, a ring, or a pin that is configured to be fixed relative to the adjacent vertebral body or other bone as the probe is advanced.

In still another example of a vertebral probe for use in spinal surgeries, the probe may comprise a shaft and a tip positioned at a distal end of the shaft and configured to penetrate a vertebral body to facilitate subsequent placement of a bone anchor providing bicortical purchase within the vertebral body. The tip and/or shaft may have any of the features and/or characteristics described throughout this disclosure, such as shafts having tapering and non-tapering sections, non-circular cross-sectioned tips, etc. The tip may be axially movable relative to the shaft. Preferably the tip comprises a non-circular shape in cross-section at least in part. In some embodiments, the tip may comprise a non-circular shape entirely and/or may comprise opposing flat surfaces that may form, for example, a "duckbill" shape.

In some embodiments, at least a portion of the vertebral probe may be spring-loaded. For example, the tip may comprise a spring-loaded tip. As another example, a bone surface engaging member, such as a pin, ring, or sleeve may be provided that may be spring loaded.

In some embodiments, the tip may be biased away from the shaft, such as by way of a spring, for example. This may allow the tip to retract relative to the shaft while the tip is advanced through cancellous bone in a vertebral body. The tip may then be configured to automatically axially protrude relative to the shaft upon breach of a distal cortical wall in the vertebral body.

Some embodiments may further comprise a sensor configured to detect a breach of the distal cortical wall during use, such as a sensor positioned adjacent to the bone engaging member and/or spring, for example.

Some embodiments may further comprise a notification means for notifying a user when a breach of the distal cortical wall has occurred. In embodiments having a sensor, the sensor may be communicatively coupled with the notification means to allow for notifying the surgeon/user upon detecting a breach with the sensor.

Some embodiments may comprise a bone engaging member configured to engage and maintain contact with a proximal cortical wall of the vertebral body as the tip advances within the vertebral body, which in some such embodiments may be spring loaded.

In some embodiments, the vertebral probe may be configured to allow for penetration of the tip through a cortical wall of a vertebral body with a first force and further configured to inhibit further advancement of the vertebral probe by requiring a second force substantially greater than the first force to achieve further advancement of the vertebral probe within the vertebral body. The tip may be blunt at the distal end of the tip (i.e., the portion that contacts bone material during use).

In some embodiments, the shaft may comprise a radiographic marker section, such as a section having a plurality of adjacent sections that vary in radiopacity.

In yet another example of a vertebral probe, the probe may again comprise a shaft and a tip positioned at a distal end of the shaft and configured to penetrate a vertebral body to facilitate subsequent placement of a bone anchor providing bicortical purchase within the vertebral body. The tip preferably comprises a non-circular shape in cross section, as described throughout this disclosure. The probe may further comprise automated means for identifying a current location of the tip within a vertebral body, such as a bone engaging member configured to engage and maintain contact with a proximal cortical wall of the vertebral body as the tip advances within the vertebral body, which may take the form of a pin, a ring, or a sleeve.

In some embodiments, the bone engaging member may be spring-loaded such that the bone engaging member is configured to be biased against the proximal cortical wall as the tip is advanced through the vertebral body.

Some embodiments may further comprise a plurality of markings configured to allow a user of the vertebral probe to determine a current depth of the tip within the vertebral body. The bone engaging member may be slidable relative to the plurality of markings to allow for visualizing a depth, or an at least approximate depth, of the probe/tip within a vertebral body or other bone.

In another example of a method for preparing a vertebral body for receipt of a bicortical bone anchor, the method may comprise advancing a tip of a vertebral probe through a proximal cortical wall of a vertebral body and then advancing the tip of the vertebral probe through cancellous bone within the vertebral body. The method may then comprise determining a depth of the tip within the vertebral body using a feature of the vertebral probe.

In some implementations, the step of determining a depth of the tip within the vertebral body using a feature of the vertebral probe may comprise inspecting a position of a bone engaging member engaging a proximal cortical wall of the vertebral body relative to an adjacent marking on the vertebral probe.

In some implementations, the step of determining a depth of the tip within the vertebral body using a feature of the vertebral probe may comprise receiving a notification from the vertebral probe indicating that the tip has breached a distal cortical wall of the vertebral body, such as actuating a light, sound, or tactile sensation, for example.

In some implementations, the vertebral probe may comprise a sensor, which may be configured to deliver a signal to a notification means to provide the notification.

The features, structures, steps, or characteristics disclosed herein in connection with one embodiment may be combined in any suitable manner in one or more alternative embodiments.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 8 is a perspective view of a vertebral probe being used to probe a vertebral body according to other embodiments;

FIGS. 9A-9C depict the probe of FIG. 8 under various radiographic views during a probing procedure;

FIG. 10A is a perspective view of another vertebral probe comprising a spring-loaded bone-engaging member for tracking a depth of the probe;

FIG. 10B is an exploded view of the probe of FIG. 10A;

FIGS. 13A-13C are cross-sectional views of another vertebral probe comprising a spring-loaded tip according to some embodiments during a vertebral probing procedure;

FIG. 21 illustrates another example of a vertebral probe according to other embodiments; and FIGS. 22A-22C depict the vertebral probe of FIG. 21 under various radiographic views during a probing procedure.

DETAILED DESCRIPTION

Figure 1:
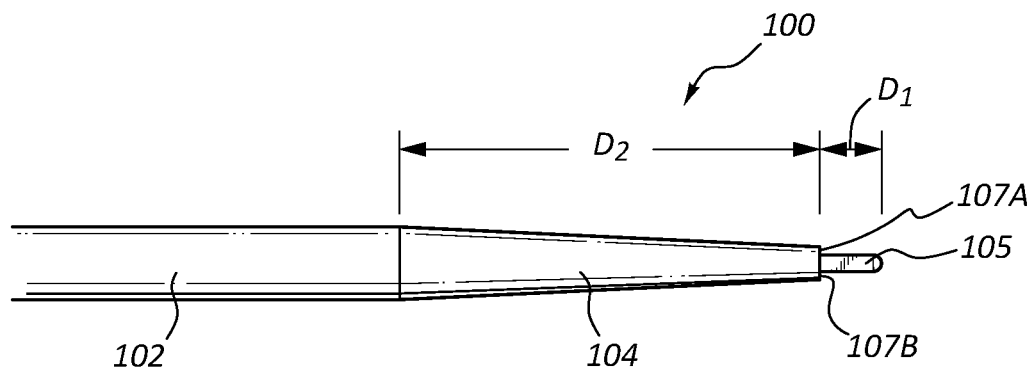
FIG. 1 is a side elevation view of a vertebral probe according to some embodiments.

It will be readily understood that the components of the present disclosure, as generally described and illustrated in the drawings herein, could be arranged and designed in a wide variety of different configurations. Thus, the following more detailed description of the embodiments of the apparatus is not intended to limit the scope of the disclosure but is merely representative of possible embodiments of the disclosure. In some cases, well-known structures, materials, or operations are not shown or described in detail.

As used herein, the term "substantially" refers to the complete or nearly complete extent or degree of an action, characteristic, property, state, structure, item, or result to function as indicated. For example, an object that is "substantially" cylindrical or "substantially" perpendicular would mean that the object/feature is either cylindrical/perpendicular or nearly cylindrical/perpendicular so as to result in the same or nearly the same function. The exact allowable degree of deviation provided by this term may depend on the specific context. The use of "substantially" is equally applicable when used in a negative connotation to refer to the complete or near complete lack of an action, characteristic, property, state, structure, item, or result. For example, structure which is "substantially free of" a bottom would either completely lack a bottom or so nearly completely lack a bottom that the effect would be effectively the same as if it completely lacked a bottom.

Similarly, as used herein, the term "about" is used to provide flexibility to a numerical range endpoint by providing that a given value may be "a little above" or "a little below" the endpoint while still accomplishing the function associated with the range.

The embodiments of the disclosure may be best understood by reference to the drawings, wherein like parts may be designated by like numerals. It will be readily understood that the components of the disclosed embodiments, as generally described and illustrated in the figures herein, could be arranged and designed in a wide variety of different configurations. Thus, the following detailed description of the embodiments of the apparatus and methods of the disclosure is not intended to limit the scope of the disclosure, as claimed, but is merely representative of possible embodiments of the disclosure. In addition, the steps of a method do not necessarily need to be executed in any specific order, or even sequentially, nor need the steps be executed only once, unless otherwise specified. Additional details regarding certain preferred embodiments and implementations will now be described in greater detail with reference to the accompanying drawings.

FIG. 1 depicts a vertebral probe 100 that may be used for various surgical procedures, such as, in preferred embodiments and implementations, scoliosis or other fusionless spinal surgeries. To provide a more particular example, probe 100 may be used to facilitate screw or other anchor placement in a vertebral body or other bone. The depicted vertebral probe 100 is specifically configured to facilitate bicortical purchase prior to placement of a vertebral screw (not shown) that extends all the way through the vertebral body—i.e., through the proximal cortical wall, through the cancellous bone, and through the distal cortical wall. Placement of screws or other anchors in this manner may be particularly useful for fusionless scoliosis surgical procedures, which typically require high strength attachment points to the spinal column and therefore often warrant use of screws that extend through two opposing cortical walls of a vertebral body. Because such procedures are typically performed in very sensitive areas of patient anatomy and can be extremely dangerous, it may be useful to provide a probe to make the screw placement procedure safer and/or easier.

Probe 100 provides various features that may be useful for these and/or other purposes. For example, probe 100 comprises a cylindrical portion 102, a tapering portion 104, and a tip 105. Tip 105 is designed to facilitate precise, safe, and/or repeatable positioning of probe 100 through a vertebral body, which may be useful to guide bone screws or other anchors through the vertebral body, particularly when bicortical purchase of the screws/anchors is required or desired.

Thus, tip 105 comprises a shape that, in at least one dimension, is less than that of the adjacent probe body (in the depicted embodiment tapering portion 104) so as to create one or more ledges or shelves 107, the purpose of which will be explained below. In the depicted embodiment, two shelves 107A and 107B are formed above and below tip 105, as shown in FIG. 1. Although for some uses it may be preferred to provide one or more sharp and/or distinct shelves, as shown in FIG. 1 (tip 105 extends at least substantially at a right angle relative to shelves 107A and 107B), it is contemplated that in other embodiments one or more tapering, smooth, and/or otherwise less sharp shelves may be formed instead. As also shown in FIG. 1, tip 105 may comprise flattened upper and/or lower surfaces so as to form a plate or plate-like shape. Thus, in some preferred embodiments, tip 105 may differ, sharply differ in some such embodiments, from the shape of the shaft of probe 100 adjacent to tip 105, which may be rounded or at least substantially rounded in cross-section.

Other tip shapes are contemplated, however. For example, in alternative embodiments, tip 105 may comprise bulbous, curved, and/or rounded surfaces. Similarly, although smooth surfaces may be preferred for certain applications and embodiments, it is also contemplated that roughened surfaces may be useful for certain procedures. Similarly, although the distal end of tip 105 is rounded, as shown in both FIGS. 1 and 2, when viewed from both the side view of FIG. 1 and the top view of FIG. 2, in other embodiments it may be desirable to form tip 105 with a sharpened distal end, which sharpening may take place in one or more dimensions so as to form, for example, either a sharpened blade-like tip or a pointed tip at the distal end of probe 100. However, for many applications it may be preferred to configure the distal end of the tip 105 specifically to avoid or be devoid of any sharp points or edges, given, for example, the nature of the delicate anatomy surrounding the vertebral column. Thus, in preferred embodiments and implementations the tip may be rounded or otherwise blunt and/or non-sharp. However, it may be provided to provide a blunt tip that is not smooth. In other words, the distal surface of the tip 105 that is configured to contact a cortical wall of a vertebral body may be surface roughened to prevent slippage.

Again, providing a blunt tip that avoids sharp points and/or edges may be desirable around sensitive patient anatomy and may be feasible due to the cortical wall of the vertebral bodies being less hard and easier to penetrate than other areas of the spine, such as the pedicle region of the spine. For similar reasons, it may be preferred to form the tip 105 and/or the entire probe as unthreaded. Thus, unlike a tap or other known devices, which may be difficult to back out and re-advance in the proper direction, providing a dull/blunt, unthreaded tip may allow for precise positioning through the cortical wall of a vertebral body and may allow for precise advancement without destroying the ability of a subsequent bone screw or other bone anchor to obtain proper purchase within the vertebral body.

One or more features of probe 100 proximal of tip 105 may also be provided to improve functionality for certain procedures, such as to prepare a vertebral body for acceptance of a bicortical-purchase screw or other bone anchor for use in, for example, fusionless scoliosis surgeries and the like. For example, the embodiment depicted in FIGS. 1 and 2 comprises a non-tapering and/or cylindrical section 102 and a tapering section 104 positioned adjacent to and distal of non-tapering section 102. As described in greater detail below, providing a tapering section 104 increases the force required in order to tamp the probe through a vertebral body or other bone portion. This may be useful to prevent the probe from being tamped too far across the vertebral body and thereby allow for greater control during the process of inserting the probe and particularly at or around the critical time of breach of the distal cortical wall, since the tapering section increases the force required for continued advancement of the probe. As also discussed further below, other embodiments are contemplated in which one or more additional non-tapering portions, preferably of specific length and positioning on the probe, are provided in order to further facilitate ease of use and/or safety.

Figure 2:
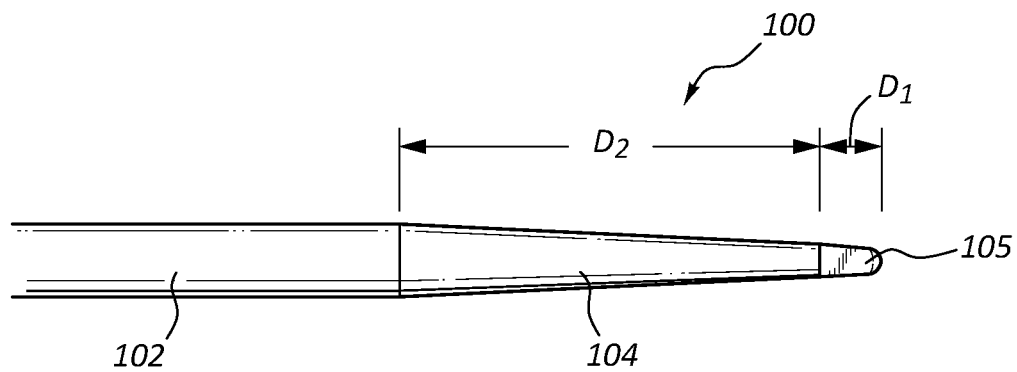
FIG. 2 is a top plan view of the vertebral probe of FIG. 1.

As shown in FIG. 2, in some embodiments, the degree of tapering on tapering section 104 may extend smoothly and apply to tip 105 when viewed from one perspective and/or in two dimensions. However, it is also contemplated that, in other embodiments, tip 105 may not be tapered in any direction/dimension or, alternatively, may taper but not smoothly with respect to tapering section 104. In other words, a ledge or shelf may be formed between tip 105 and an adjacent section, whether tapering or not, when viewed from any perspective. In other words, in some such embodiments, the shelf/ledge may extend about the entire perimeter of tip 105 or may extend about the perimeter of tip 105 along all but one side of tip 105, if desired.

The dimensions of various portions of probe 100 may also be important and may be related to particular dimensions of patient anatomy, such as the dimensions of a vertebral body and/or a specific portion/aspect of a vertebral body. For example, again with reference to FIGS. 1 and 2, there may be some preferences in terms of dimensions D1 and D2 that may impact functionality. In preferred embodiments, distance D1 may be at least as long as the distance between opposing outer cortical walls of a particular vertebral body through which the probe is to be inserted. In some such embodiments, distance D1 may be the same, or at least substantially the same, as this distance. Thus, distance D1 may vary depending upon the particular patient and/or the particular vertebral body that is to the subject of a surgical procedure.

Thus, it is contemplated that some embodiments may comprise a set of probes having different dimensions according to a particular portion of the vertebral column, such as a thoracic probe (22-35 mm) and a lumbar probe (35-45 mm). In some particularly preferred embodiments that may be generally useful for a variety of different patient anatomies, however, D2 may be between about 22 and about 35 mm for a thoracic probe and may be between about 35 and about 45 mm for a lumbar probe. Thus, more generally speaking, in certain preferred embodiments, distance D2 may be between about 20 and about 50 mm. In some such embodiments, distance D2 may be between about 22 and about 45 mm.

Similarly, although there are preferred ranges for distance D2, this distance may also vary depending upon the patient and portion of the vertebral column being probed. However, in some particularly preferred embodiments that may be generally useful for a variety of different patient anatomies, D2 may be between about 2 and about 3 mm for a thoracic probe and may be between about 3 and about 5 mm for a lumbar probe. Thus, more generally speaking, in certain preferred embodiments, distance D1 may be between about 2 and about 6 mm. In some such embodiments, distance D1 may be between about 3 and about 5 mm.

Other dimensions of probe 100 may be significant as well. For example, as previously mentioned, at least one dimension of tip 105 is preferably less than that of the adjacent portion/section of probe 100 so as to provide one or more shelves, ledges, or other features—such as shelves 107A and 107B—for providing tactile sensation indicative of probe location, as described below, and/or controlling advancement of probe 100. In addition, preferably tip 105 and/or the remaining portion of probe 100 that is configured and/or designed to extend through bone comprises a maximal cross-sectional dimension that is less than the major diameter of a thread depth of a bone screw of which probe 100 is being used to facilitate entry. It may also be preferred that, in certain embodiments, tip 105 comprises a maximal cross-sectional dimension that is less than a major diameter and/or maximal cross-sectional dimension of a tip of such bone screw.

Further, although the distal end of tip 105 is depicted as rounded, it is contemplated that, in alternative designs, providing a flattened distal end, or an at least substantially flattened distal end, may be advantageous for certain purposes.

Figure 3A:
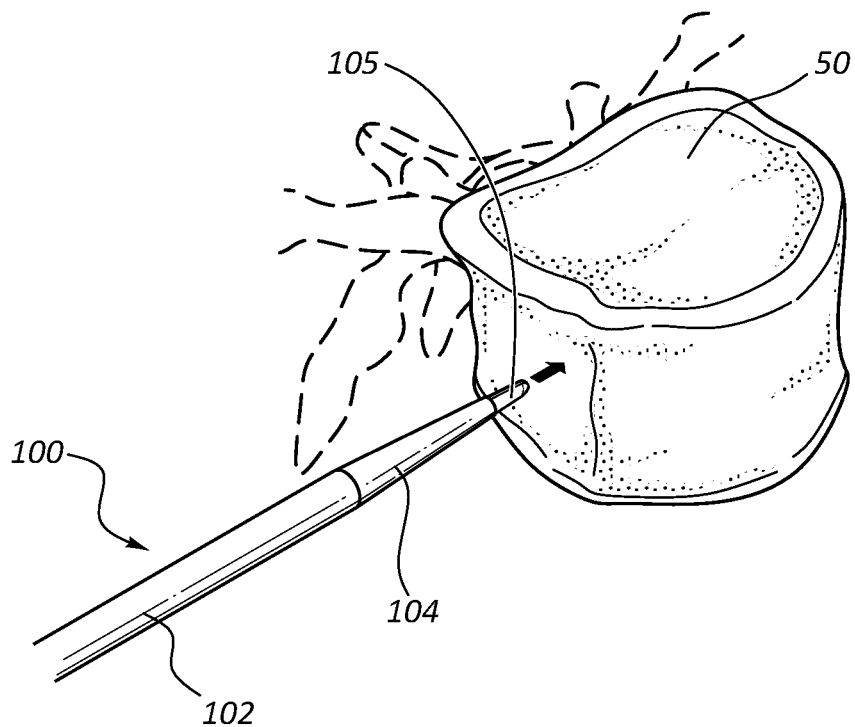
FIG. 3A is a perspective view of the vertebral probe of FIGS. 1 and 2 being advanced against the proximal vertebral cortex.

FIGS. 3A-3D depict various steps/stages during a process for using probe 100 according to certain preferred implementations of inventive methods. In FIG. 3A, tip 105 of probe 100 is advanced to contact a proximal cortical wall of a vertebral body 50. Because tip 105 is smaller than the rest of probe 100, a smaller, less invasive opening 55 (see FIG. 3B) may be formed by tamping or otherwise advancing tip 105 only through the proximal cortical wall of vertebral body 50.

Figure 3B:
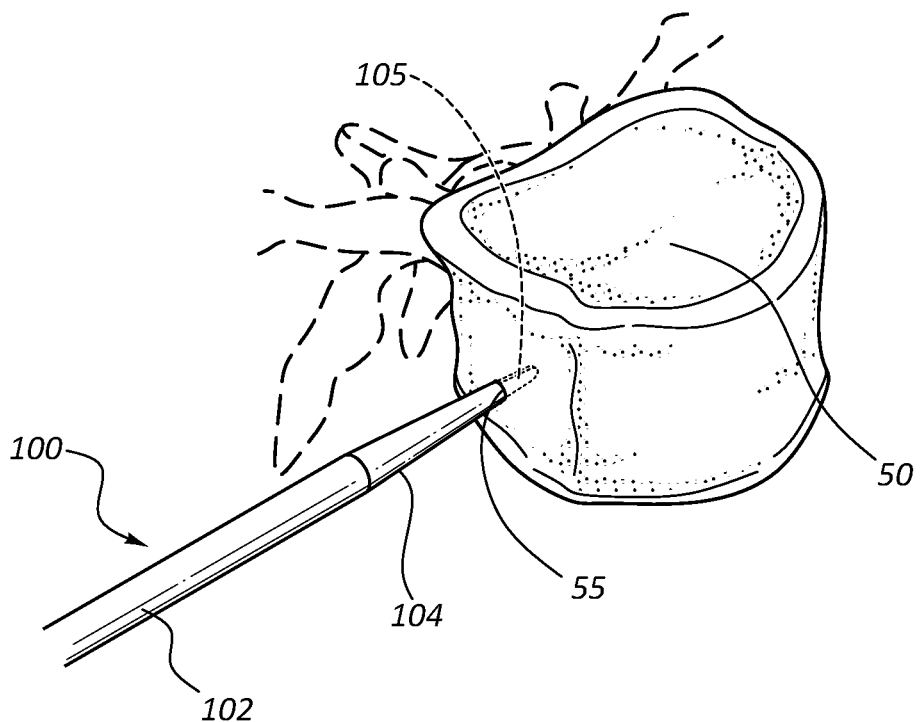
FIG. 3B is a perspective view of the vertebral probe of FIGS. 1 and 2 following penetration of a tip of the vertebral probe through the proximal vertebral cortex.

FIG. 3B depicts probe 100 following the formation of an opening in the proximal cortical wall of vertebral body 50 by tip 105. Due to the presence of one or more shelves 107, after tip 105 penetrates the cortical wall, a relatively large differential in force is required to advance probe 100 further due to the blunt shelf 107 contacting the dense cortical bone. Moreover, a surgeon may be able to, by tactile feel alone, confirm that the probe 100 is in the position depicted in FIG. 3B with the tip 105 extending into the vertebral body and the shelf 107 inhibiting further penetration.

Figure 3C:
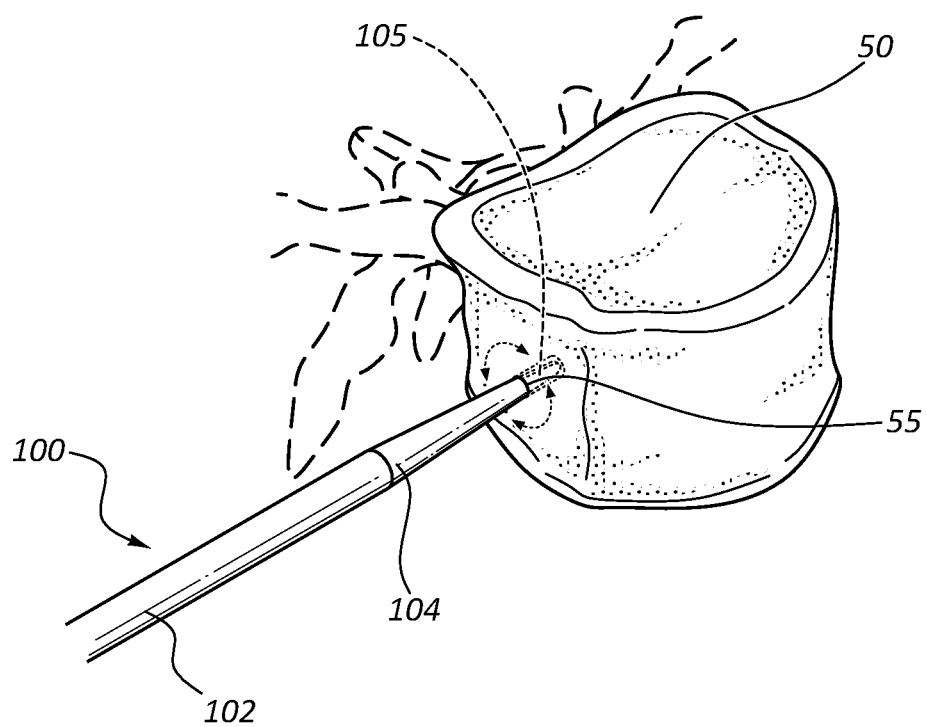
FIG. 3C is a perspective view of the vertebral probe of FIGS. 1 and 2 during the process of rotating the probe to create a chamber for further receipt of the probe therein.
Figure 6:
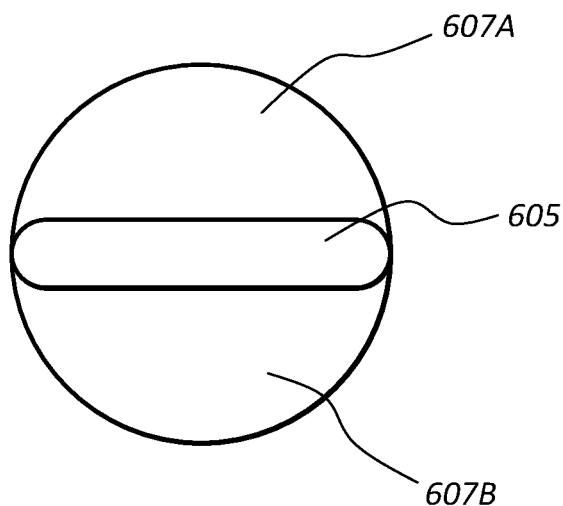
FIG. 6 is a side elevation view of a tip of a vertebral probe viewed along an elongated axis of the probe according to some embodiments.

FIG. 3C depicts the probe 100 being rotated to form a chamber with tip 105 that is circular, or at least substantially circular. This step may be performed once it has been determined that the initial penetration of the vertebral wall is in a suitable position to guide a bone screw or other anchor therethrough. Rotating the tip 105 in this manner may facilitate further penetration of probe 100 into the vertebral body 50 by providing less resistance to further tamping and/or advancement of probe 100. In some embodiments and implementations, the chamber formed by tip 105 may have the same, or at least substantially the same, diameter as the portion of the shaft immediately adjacent to tip 105. Thus, in such embodiments and implementations, the tip 105 may have a width that extends all of the way, or at least substantially all of the way, along the diameter of the adjacent shaft, as shown in FIG. 6.

Figure 3D:
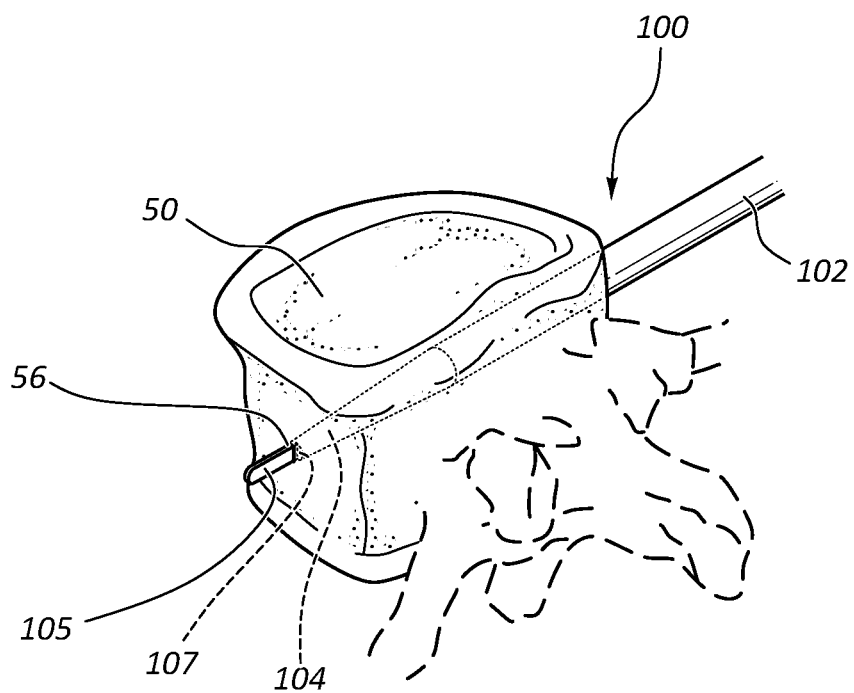
FIG. 3D is a perspective view of the vertebral probe of FIGS. 1 and 2 following penetration of the tip of the vertebral probe through the distal vertebral cortex.

FIG. 3D depicts probe 100 after it has been fully extended through opposing cortical walls of vertebral body 50. Thus, in addition to proximal opening 55, a distal opening 56 through the distal cortical wall is formed by tip 105. As previously mentioned, tapering portion 104 preferably extends through the entire, or at least substantially the entire, length of at least the cancellous bone of vertebral body 50, so as to provide continued resistance during tamping/advancement of probe 100 and prevent the probe from extending too far into and/or through vertebral body 50.

As also illustrated in FIG. 3D, shelf 107 is in contact with the inner cortical wall of vertebral body 50. Again, as discussed in connection with the penetration of probe 100 through the proximal cortical wall, shelf 107 may prevent or at least inhibit further advancement of probe 100 after tip 105 has extended through the distal cortical wall and/or may provide a surgeon with a tactile sensation to indicate the position of probe 100 illustrated in FIG. 3D. Thus, by providing a length of tip 105 that takes into account the available space adjacent to a particular vertebral body, the probing procedure and/or the following bone screw placement procedure may be made safer and more precise.

Although not shown in the figures, it is also contemplated that probe 105 may be rotated again following penetration through the distal cortical wall, similar to the rotation discussed above in connection with FIG. 3C. This may provide for a rounded hole that may be more suitable for guidance of the tip of a bone screw or anchor for bicortical screw purchase.

Figure 4:
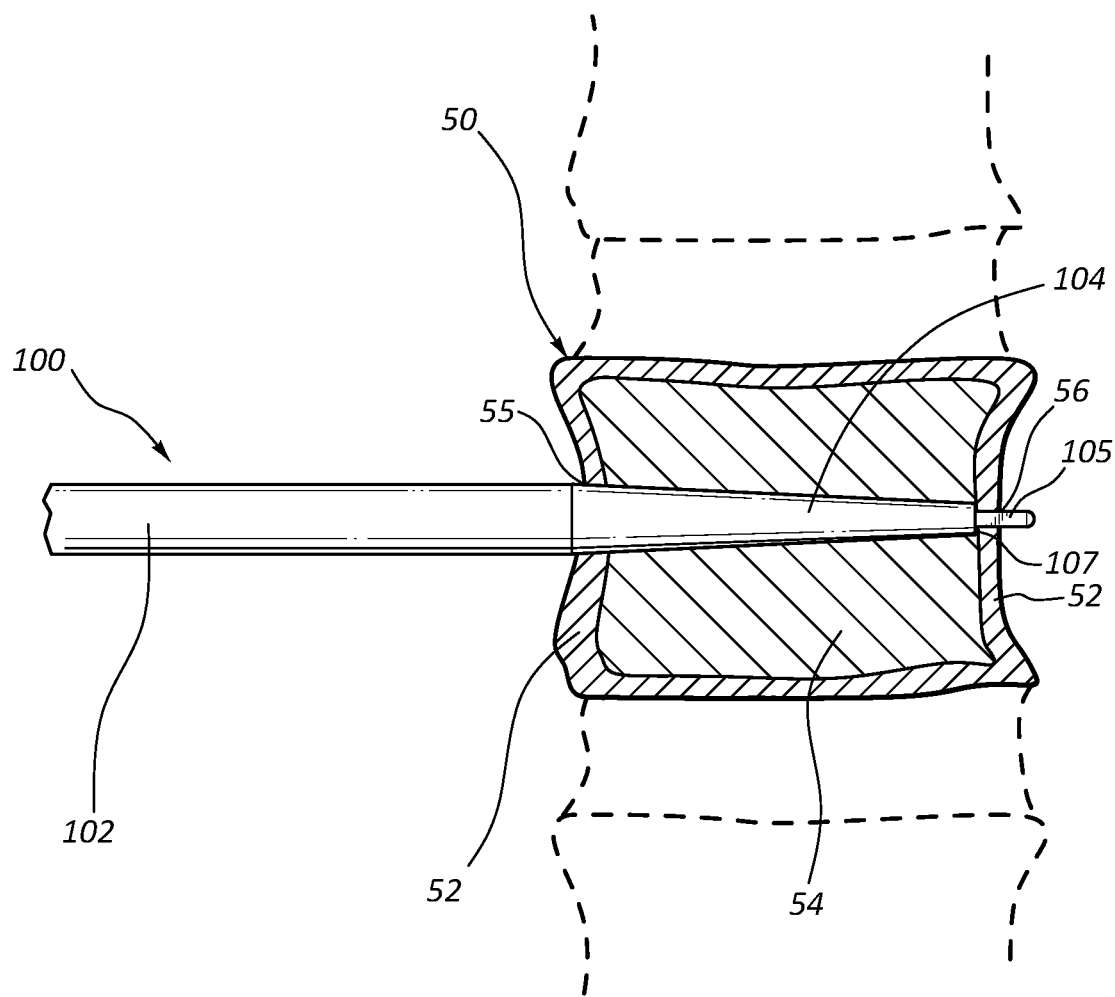
FIG. 4 is a cross-sectional view of a vertebral probe according to some embodiments fully extending through a vertebral body with the probe tip extending through the distal vertebral cortex of the body.

FIG. 4 is a cross-sectional view of probe 100 fully extended through vertebral body 50 with shelf 107 contacting the inner cortical wall 52 and tapering portion 104 extending through the cancellous core 54 of vertebrae 50. As shown in this figure, tapering portion 104 is configured to match, or at least substantially match, the width of vertebrae 50 in that it terminates just outside the proximal opening 55 in cortical shell 52. However, other embodiments are contemplated that may include non-tapering portions configured to extend into a vertebral body, as discussed below, or that taper along the entire length of the probe.

Figure 5:
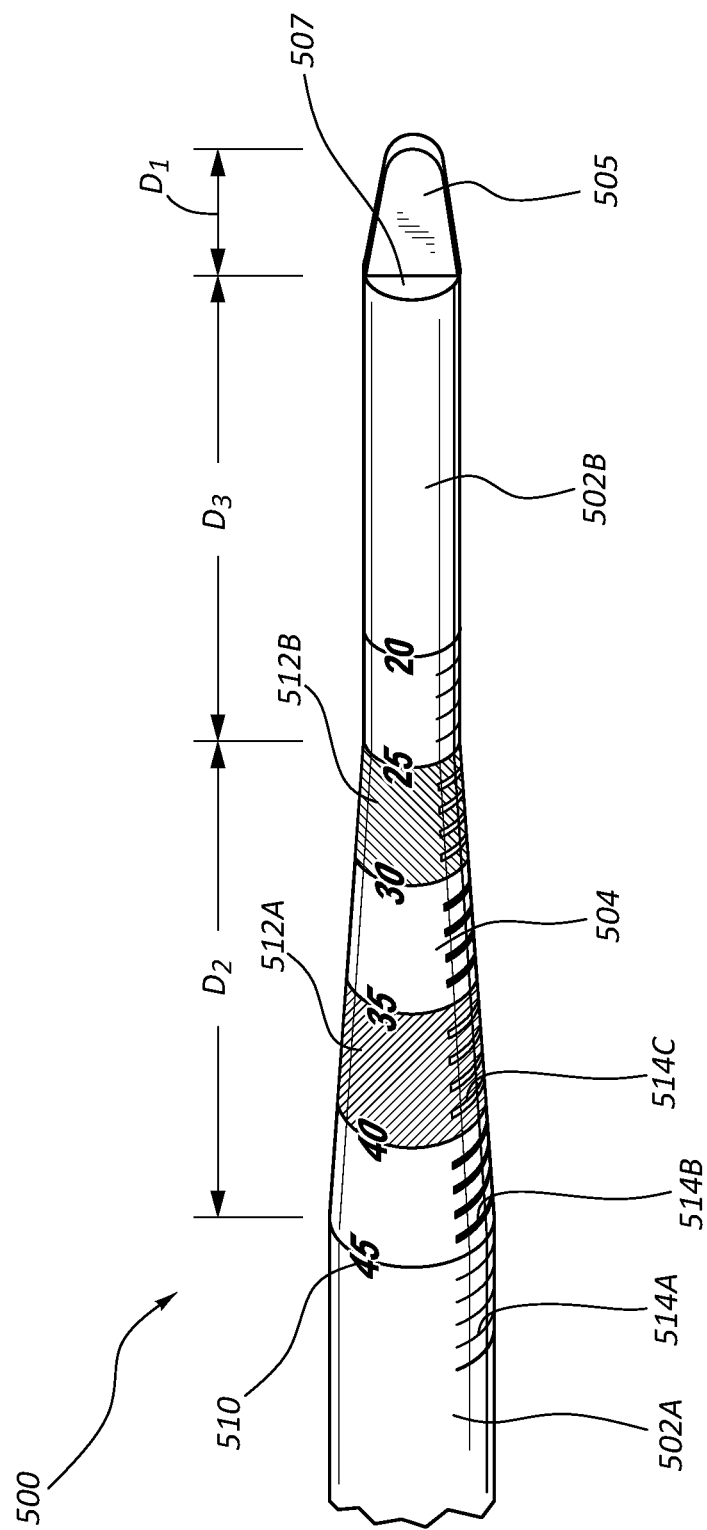
FIG. 5 depicts a vertebral probe according to other embodiments.

FIG. 5 depicts a vertebral probe 500 according to other embodiments. Probe 500 differs from probe 100 in several respects, any one or more of which may be applied to probe 100, or vice versa, in a piecemeal fashion as desired. First, probe 500 comprises two non-tapering portions, namely, a first or proximal non-tapering portion 502A and a second or distal non-tapering portion 502B. A tapering portion 504 is positioned in between non-tapering portions 502A and 502B.

Non-tapering portion 502B is configured to extend through a vertebral body during a probing procedure. Providing one or more such non-tapering portions may be useful to allow for easier penetration/excavation during this procedure, but preferably only for a precise, predetermined length that may be dictated by and/or correspond with the anatomy of the vertebral body being probed.

The tamping or other advancement of probe 500 may then be slowed by providing an adjacent tapering portion 504, which may add to the force required to advance the probe 500 further. The degree of force added may be proportional to the degree of tapering and may vary as desired depending upon other features of the probe, the structure of the vertebrae, and/or surrounding patient anatomy.

As mentioned above, the lengths of various sections of probe 500 may also vary in accordance with patient anatomy. For example, in some embodiments, non-tapering section 502B may comprise a distance D3 of between about 12 mm and about 20 mm for a small probe (with a more preferred distance being about 16 mm), between about 18 mm and about 25 mm for a medium probe (with a more preferred distance being about 21 mm), and between about 23 mm and about 30 mm for a large probe (with a more preferred distance being about 26 mm). Tapering section 504 may comprise a distance D2, which may be any desired length but preferably sufficiently long such that when probe 500 is fully positioned through a vertebral body with the tip protruding through the distal cortical wall, tapering section 504 is long enough to extend through the proximal cortical wall opening to provide resistance to advancement of the probe 500 during and/or prior to breach of the distal cortical wall.

Some embodiments may provide for a series of probes for use in connection with different patients and/or different vertebral bodies. However, in preferred embodiments and implementations, the "working section" of the probe (in other words, the portion of the probe that will enter the vertebrae), may be specifically tailored to the typical width of a vertebrae and therefore may have various distances that are proportional to one another. For example, in some embodiments, the distance D3 may be between about five and about seven times the length of D1. In this manner, the tapering section, which may act to inhibit advancement of the probe within a vertebral body, may begin at or near the point at which the tip makes contact with the inner surface of the distal cortical wall, which may provide enhanced safety and provide a surgeon with a tactile feel that is associated with this portion of the advancement. Similarly, in some embodiments, D1 may be between about 10 and about 25% of the length of D3.

As mentioned above in connection with probe 100, probe 500 further comprises a tip 505 defined in part by shelf 507. Again, tip 505 is preferably configured to allow for penetration through a cortical wall or other high-density bone portion and substantially increase the amount of force required to advance probe 500 further by providing a shelf for contacting this high-density wall. Thus, a surgeon will preferably be able to feel when shelf 507 has contacted both the proximal and distal cortical walls to assist in precise and safe placement of the probe and the subsequent bone screw/anchor. As also previously mentioned, distance D1 of tip 505 may be between about 2 and about 3 mm for a thoracic probe and may be between about 3 and about 5 mm for a lumbar probe. Thus, more generally speaking, in certain preferred embodiments, distance D1 may be between about 2 and about 6 mm. In some such embodiments, distance D1 may be between about 3 and about 5 mm.

Probe 500 also comprises several other features not shown or described in connection with probe 100. For example, probe 500 comprises a series of markings configured to further facilitate ease of use, safety, and/or subsequent screw/anchor placement. More particularly, probe 500 comprises a series of alphanumerical markings 510 along with a series of more precise markings (dash lines in the depicted embodiment) that may allow a surgeon to take very precise measurements of the vertebral anatomy and/or receive a very precise indication of the current placement of the probe 500.

In some embodiments, a series of adjacent sections comprising distinct markings of one or more types may be provided. Thus, probe 500 comprises a first series of dash lines 514A comprising relatively thin lines, a second series of dash lines 514B adjacent to the first series 514A comprising relatively thicker lines, a third series of dash lines 514C comprising still different dash lines (of a different color), and so on. By varying the sections, a surgeon may be provided with a more general view, once the surgeon becomes familiar with the marking system, of the probe 500 placement without having to rely on the alphanumerical markings 510, which may be most useful following full advancement of the probe 500 to provide the surgeon with a very precise indication of the width of the vertebral body to allow for screw selection.

Other distinct patterns/sections may be provided, either in addition to or as an alternative to those mentioned above. For example, in the depicted embodiment, two or more adjacent sections may be colored, patterned, and/or otherwise marked distinctly. Thus, each of the sections in between adjacent alphanumerical markings 510 may be colored, patterned, and/or otherwise marked distinctly. As shown in the figure, section 512A may therefore comprise a first color and section 512B may comprise a second color distinct from the first color. Sections immediately adjacent to sections 512A and 512B may similarly be visibly distinct from their adjacent sections. Thus, these sections are depicted as uncolored in the embodiment of FIG. 5. These more general markings may allow a surgeon to easily and immediately receive a general indication of the extent to which the probe 500 has penetrated a vertebral body. For example, a green section may indicate that the probe is in a central location within the vertebral body, a yellow section may indicate that the distal cortical wall is approaching, and a red section may indicate danger, such as that the probe is near or beyond the distal cortical wall. In some contemplated embodiments, one or more of these marking features may therefore be provided without the novel probe tip 505 disclosed herein.

Of course, those of ordinary skill in the art will appreciate a variety of alternative configurations to allow a surgeon to visualize an approximate location of a vertebral probe within a vertebral body without requiring precise numerical measurements and/or tick marks. Thus, the adjacent sections 512 with distinct markings spanning multiple more precise markings and the distinct patterns of dash lines 514 between adjacent sections are examples of means for coarsely visualizing a current location of a vertebral probe within a vertebral body. As mentioned above, the finer measurements provided by dash lines 514 may then be used, for example, to provide a precise measurement of the span of a vertebral body, which may be useful for bone screw selection.

In preferred embodiments, the markings on the probe may be visible from every side and/or angle of the probe. Thus, for example, duplicate markings may be positioned on the opposite side, or more than two sets of such markings may be provided. Similarly, in some embodiments, some or all of the markings may be staggered so that each marking is positioned slightly above or below the adjacent markings such that the markings gradually rotate about.

FIG. 6 is an axial, front elevation view of a tip 605 of a vertebral probe according to some embodiments. As shown in this figure, tip 605 comprises flattened upper and lower surfaces and these surfaces may extend smoothly on the sides into the body of the probe. Thus, this design provides upper and lower shelves 607A and 607B, respectively, which, as discussed above, facilitate positioning of a probe through proximal and/or distal cortical walls adjacent to tip and may provide for tactile feel of such probe position.

Figure 7:
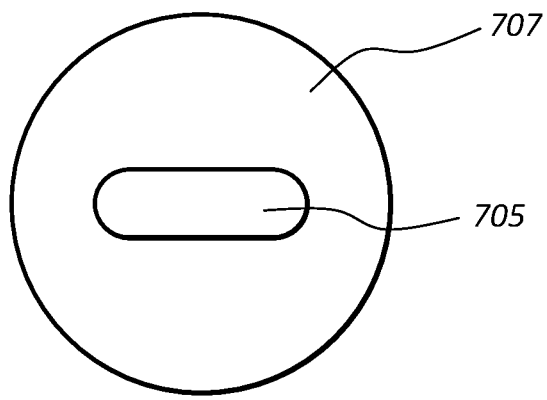
FIG. 7 is a side elevation view of another tip of a vertebral probe viewed along an elongated axis of the probe according to still other embodiments.

Alternatively, however, as shown in the axial, front elevation view of FIG. 7, the tip 705 may protrude from a central region of a single shelf 707. Still other embodiments are contemplated. For example, the sides of the probe tip may taper towards a rounded or pointed tip to form a tongue-like shape or may extend parallel to one another to form more of a table-top shape if desired.

However, it is contemplated that other non-symmetrical shapes may be used for vertebral probe tips, as desired. Thus, it may be preferred to have a probe body comprising a circular shape in cross-section with a tip that comprises a non-circular and/or non-symmetrical shape in cross-section, if not the flattened or "duckbill" shapes depicted in the figures.

Still another embodiment of a probe 800 is illustrated in FIG. 8. Probe 800 again comprises a shaft having a cylindrical portion 802, a tapering portion 804, and a tip 805. Tip 805 may be similar in shape and function to those discussed above and therefore may have a shape that, in at least one dimension, is less than that of the adjacent probe body so as to create one or more ledges or shelves and/or may comprise flattened upper and/or lower surfaces so as to form a plate or plate-like shape. However, probe 800 also comprises a sensor 820 that may be configured to sense one or more variables to allow for automated and/or electronic confirmation of the current position of the probe within a bone.

For example, in some embodiments, sensor 820 may be configured to sense the density of the bone at the tip 805 and/or another suitable location along probe 800, which may allow for distinguishing between the cortical wall of a vertebral body and the inner cancellous bone, and/or to sense the depth with which the probe has penetrated the vertebral body or other bone. In some such embodiments, the sensor 820 may be configured to measure electrical conductivity of the bone to differentiate between cortical bone, cancellous bone, and potentially other tissue, such as blood and/or nerve tissue. An example of such a sensor can be found in U.S. Pat. No. 7,580,743 titled "Device for Monitoring Penetration into Anatomical Members," which patent is incorporated by reference herein in its entirety. Another example of sensing technology that may be incorporated into a vertebral probe according to some embodiments can be found in U.S. Pat. No. 8,419,746 titled "Exploration Device to Monitor the Penetration of an Instrument in an Anatomic Structure," which is also hereby incorporated by reference in its entirety.

It should be understood, however, that the uses for the probes in these references are distinct from preferred embodiments of the present invention. For example, the PediGuard® probe is used for placement of pedicle screws. The goal of this devices is to avoid penetration through the cortical wall of the pedicle by providing notifications when the probe contacts cortical bone. By contrast, in certain preferred embodiments of the inventions disclosed herein, the goal would be to penetrate cortical bone at opposite sides of the vertebrae (to facilitate placement of bicortical purchase vertebral anchors) but avoid having the probe extend to far through the distal cortical wall, where critical anatomical features are located. Thus, although similar sensor technology to the PediGuard® probe may be used in connection with some embodiments of the invention, the way the sensor is used to provide notifications to the user in such embodiments may be quite different. For example, as discussed throughout this disclosure, the probe may be configured to alert the user to a breach of the distal cortical. Of course, as those of ordinary skill in the art will appreciate, some embodiments may further be configured to notify a user when the probe has made contact with the distal cortical wall so that a user can be prepared for the breach, which may provide a more emphatic warning to the user than the initial, cortical contact notification in some embodiments (or the only notification in other embodiments).

Probe 800 further comprises one or more means for visually and/or audibly notifying a surgeon or practitioner as to the density of the bone at the tip 805 and/or sensor 820 and/or as to the position of the tip 805 and/or sensor 820 within a vertebral body 50 or other bone. For example, probe 800 comprises a display 822, which may comprise, for example, one or more LEDs or other lights and in some embodiments may comprise a speaker 824 for providing an audible alert. In some embodiments and implementations, probe 800 may therefore be configured to provide a visual and/or audible alert when tip 805 of probe 800 is at or near a cortical bone region, such as when tip 805 is at or near the distal cortical wall of vertebral body 50, which may provide for enhanced patient safety during a probing procedure, which, as discussed above, may take place prior to positioning of a screw or other bone anchor, such as a bicortical bone anchor, during a fusionless or other spinal surgery. A switch, button, or other actuation means 826 may also be provided to turn sensor 820, display 822, and/or speaker 824 on or off as desired.

FIG. 8 also illustrates the possible use of various x-ray images that may be taken along mutually perpendicular axes, such as the indicated x, y, and z axes. FIGS. 9A-9C illustrate possible views of the probe 800 that may be used to verify the position thereof during a probing procedure. To allow for such visualization, some embodiments may utilize, either in whole or in part, a radio-opaque material for the probe. However, it is contemplated that, in some embodiments, due to one or more of the unique safety features presented herein, some embodiments may be configured to allow a surgeon to perform the probing procedure without use of x-ray or other imaging techniques.

FIGS. 10A and 10B illustrate yet another example of a vertebral or other bone probe 1000. Probe 1000 comprises several features previously mentioned, including a shaft having a cylindrical/non-tapering portion 1002, a tapering portion 1004, and a tip 1005, which, again, may be similar in shape and function to those discussed above and therefore may have a shape that, in at least one dimension, is less than that of the adjacent probe body so as to create one or more ledges or shelves and/or may comprise flattened upper and/or lower surfaces so as to form a plate or plate-like shape.

Probe 1000 further comprises an automated means for identifying a current location of the tip 1005 or another portion of probe 1000 within a vertebral body or other bony structure. However, the means provided for in this embodiment is mechanical and need not rely on a sensor. More particularly, probe 1000 comprises a bone engaging member 1020, which, as discussed in greater detail below, may be configured to engage a proximal cortical wall of a vertebral body and, as tip 1005 passes through the inner/cancellous portion of the vertebral body, preferably maintains contact with this cortical wall but is movably engaged with at least a portion of the shaft to allow for visualization of the depth of penetration of tip 1005 within the vertebral body.

In the depicted embodiment, bone engaging member 1020 comprises a pin 1020 that is slidably positioned within a slot or window 1021 formed in a portion of the shaft of probe 1000. A spring 1022 may be provided to allow bone engaging member 1020 to preferably be biased towards a distal direction such that bone engaging member 1020 maintains contact with, for example, the proximal cortical wall of a vertebral body while the tip 1005 is advanced through the vertebral body.

In the depicted embodiment, probe 1000 comprises an inner rod 1025 that is slidably engaged with an outer shaft portion 1027. Inner rod 1025 may be fixedly coupled with bone engaging member 1020, which may extend at an angle, such as a perpendicular or at least substantially perpendicular angle in some embodiments, from the elongated axis of inner rod 1025. Because inner rod 1025 is slidable relative to outer shaft portion 1027, movement of outer shaft portion 1027, which may be threadably or otherwise fixedly coupled with tip 1005, within a vertebral body or other bone may result in movement of tip 1005 therethrough while inner rod 1025 and bone engagement member 1020 remain fixed relative to the adjacent vertebral body/bone structure. Thus, by providing a series of markings 1010, such as dash lines and/or adjacent alphanumerical markings, on outer shaft portion 1027, a surgeon may be able to visualize the depth with which tip 1005 has penetrated and/or another portion of probe 1000 has penetrated vertebral body 50 or another bone.

A second slot or window 1031 may be formed along a more proximal portion of the outer shaft portion that would typically not penetrate the vertebral body 50, preferably adjacent to markings 1010. A visually-recognizable feature 1029, such as a marking, groove, or protrusion, for example, may be positioned on rod 1025 such that, as tip 1005 extends through the vertebral body, feature 1029 moves relative to window/slot 1031 to allow markings 1010 adjacent to feature 1029 to indicate the position of the tip 1005. In some embodiments, markings 1010 may include various colors and/or sections to be used as an indicator that the tip 1005 is likely at or very close to the distal cortical wall, which may allow a surgeon to reduce the amount of force currently being used to advance probe 1000 as a safety measure.

Figure 11A:
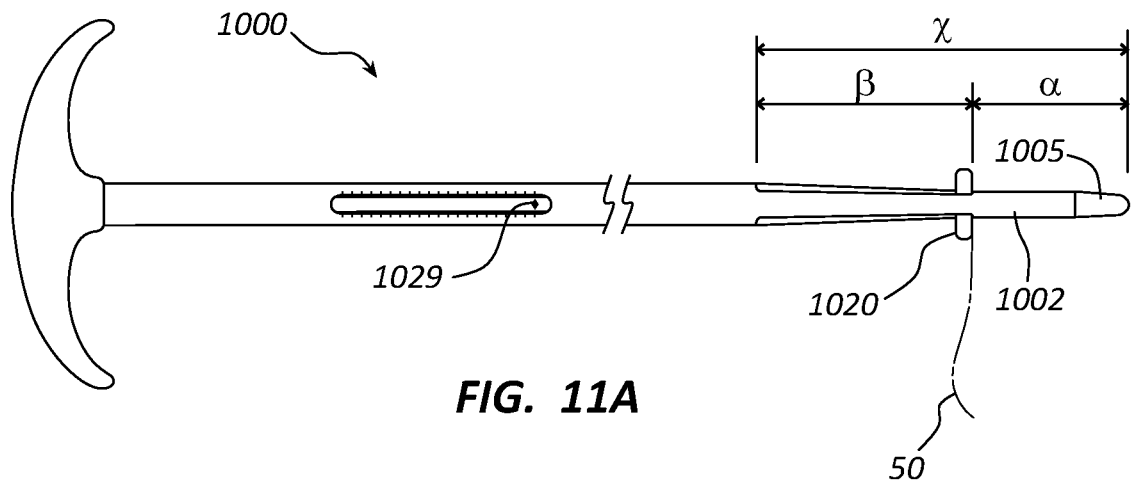
FIGS. 11A-11C depict additional views of the probe of FIGS. 10A and 10B during various stages of a probing procedure within a vertebral body.
Figure 11B:
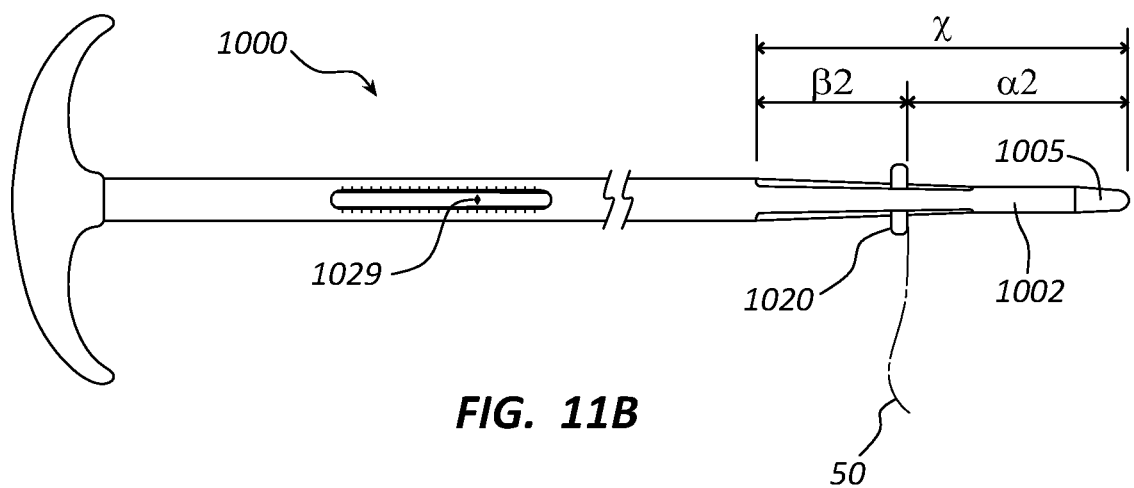
Figure 11C:
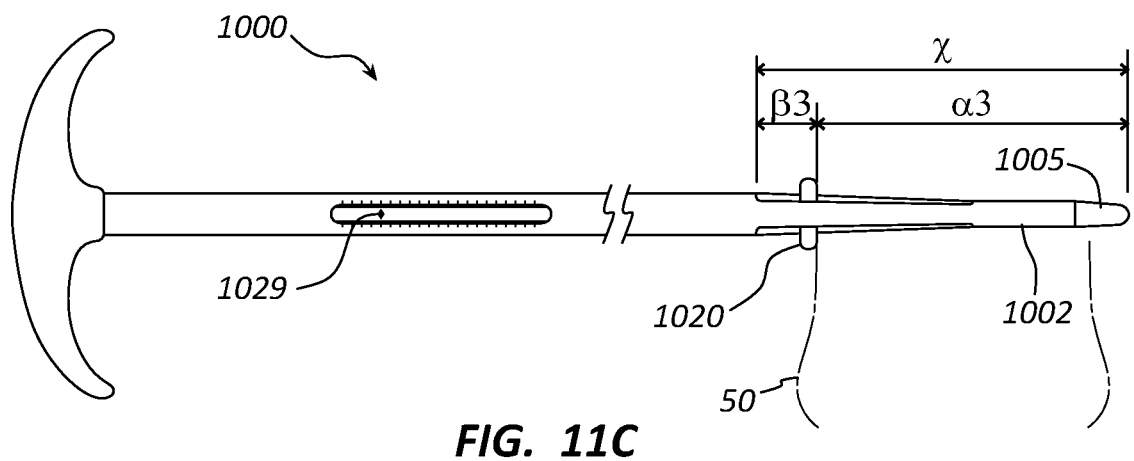

FIGS. 11A-11C illustrate various steps during a probing procedure during which probe 1000 is inserted within a vertebral body 50 to prepare for placement of a bone screw therein. In particular, as shown in FIG. 11A, once engaging member 1020 has contacted the proximal cortical wall of vertebral body 50, tip 1005 can continue to advance while engaging member 1020 is prevented from further advancement, which results in movement of feature 1029 with respect to the outer portion of the shaft of probe 1000 and the markings 1010 provided thereon. Thus, the two distances making up distance x from the distal end of tip 1005 to the proximal end of the moveable path of engaging member 1020, namely, distance α from the distal end of tip 1005 to engaging member 1020 and distance 13 from engaging member 1020 to the proximal end of the moveable path of engaging member 1020, change to α2 and β2 and α3 and β3, respectively, as shown in FIGS. 11B and 11C as the tip 1005 of probe 1000 is advanced. Due to the corresponding movement of feature 1029, a surgeon or other user is able to identify the depth with which tip 1005 has advanced, in some cases without use of additional technology such as radiography. Distance β may also represent the length of the slot 1021 within which bone engaging member 1020 slidably extends, which may comprise, for example, a distance of between about 20 mm and about 40 mm. Similarly, distance α may comprise, for example, a distance of between about 15 and about 25 mm.

Figure 12A:
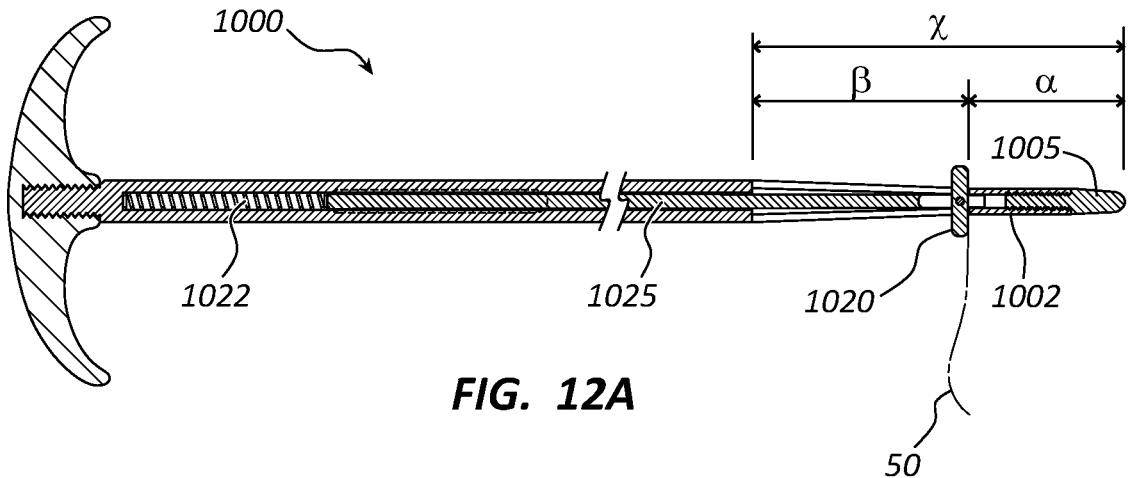
FIGS. 12A-12C are cross-sectional views of the probe taken from FIGS. 11A-11C, respectively.
Figure 12B:
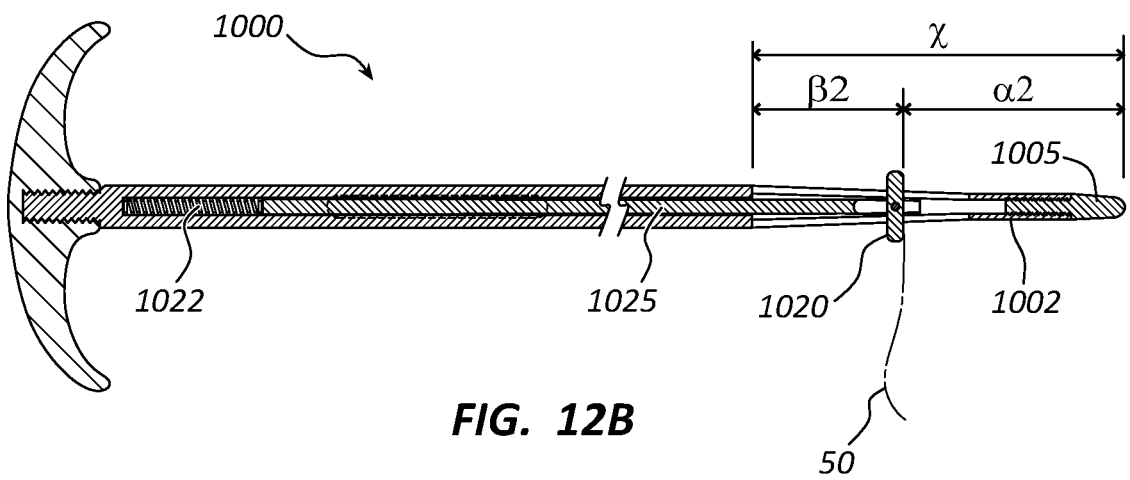
Figure 12C:
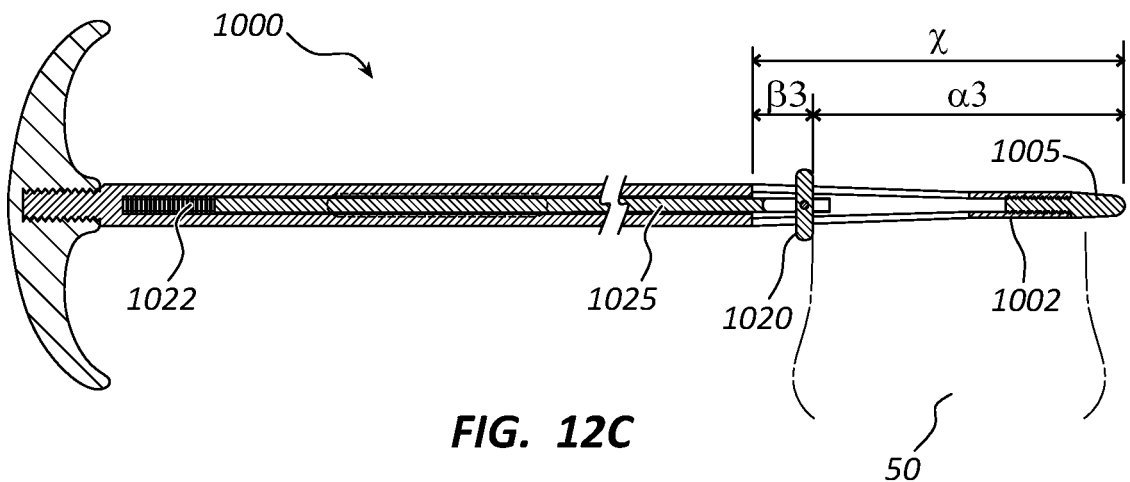

FIGS. 12A-12C illustrate the same series of steps during a probing procedure using probe 1000 but are taken in cross-section to illustrate the inner workings of probe 1000. In particular, it can be seen in these figures that, as engaging member 1020 makes contact with the proximal cortical wall of vertebral body 50, inner rod 1025 compresses spring 1022, which may be beneficial to ensure that engaging member 1020 maintains contact with the proximal cortical wall or other external bone surface to maintain accuracy of the depth measurements provided by probe 1000.

Still another embodiment of a probe 1300 is shown in FIGS. 13A-13C, which is shown in cross section during a probing procedure. As shown in these figures, probe 1300 may comprise one or more of the features previously mentioned, such as a shaft having a cylindrical portion 1302, a tapering portion 1304, and a tip 1305, which, again, may be similar in shape and function to those discussed above and therefore may have a shape that, in at least one dimension, is less than that of the adjacent probe body so as to create one or more ledges or shelves and/or may comprise flattened upper and/or lower surfaces so as to form a plate or plate-like shape.

However, rather than having a spring-loaded depth/bone engaging feature, such as engaging member 1020 of probe 1000, probe 1300 comprises a spring-loaded tip 1305 which may be configured to compress as tip 1305 is being advanced through a vertebral body 50 or other bone and then spring out a predetermined distance once the distal cortical wall of the vertebral body 50 or other bone portion has been breached. Thus, to explain with more particularity, probe 1300 comprises an inner rod or shaft 1325 that is slidably positioned within the outer portion of the shaft. Inner rod 1325 is coupled with tip 1305. Thus, upon contacting the distal cortical wall, as shown in FIG. 13B, spring 1322 is compressed and tip 1305 is positioned flush with the adjacent portion of the outer shaft. Once the distal cortical wall has been breached, as shown in FIG. 13C, spring 1322 advances tip 1305 by a precise amount, which may ensure that the tip 1305 is not advanced too far, again, largely due to the very delicate and critical tissues in the surrounding regions. A handle 1340 of any suitable shape and size may also be provided. Also, although spring 1322 is shown, as those of ordinary skill in the art will appreciate, other embodiments are contemplated in which other biasing means for biasing the tip 1305 distally with respect to an adjacent portion of the probe 1300 may be used in alternative embodiments.

It may also be preferred in some embodiments to include a sensor and/or sensor assembly 1320 that may detect when the distal cortical wall has been breached. This may take place, for example, by detecting when spring 1322 has relaxed and/or when spring 1322 spikes in its length and/or state of contraction. In some embodiments, the sensor assembly 1320 may comprise, for example, a magnetic sensor that may be used to detect a given amount of movement of spring 1322. Alternatively, sensor/sensor assembly 1320 may be placed at any other desired and feasible location on probe 1300. Similarly, the sensor/sensor assembly may be replaced with an alternative sensor/sensor assembly, including but not limited to any of the other sensors referenced herein. A signal from the sensor 1320 may be delivered, either via a wire or wirelessly, to any suitable alarm, display, or other output, as desired, including but not limited to any of the displays and/or or other notification means disclosed herein. In this manner, a user may be notified, such as by way of any of the notification means disclosed herein, that the distal cortical wall has been breached.

Figure 14A:
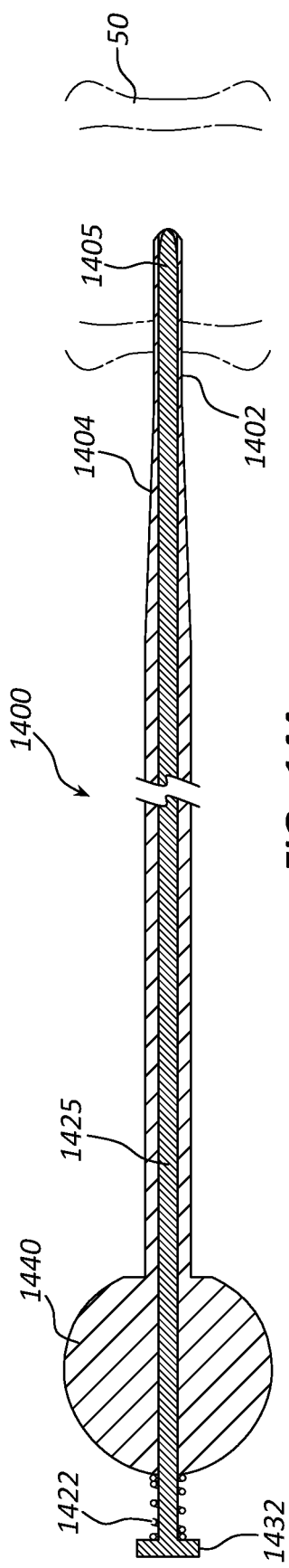
FIGS. 14A-14C are cross-sectional views of a vertebral probe according to other embodiments in which a spring-loaded cortical wall punch is provided to breach the distal cortical wall by a predetermined amount.
Figure 14B:
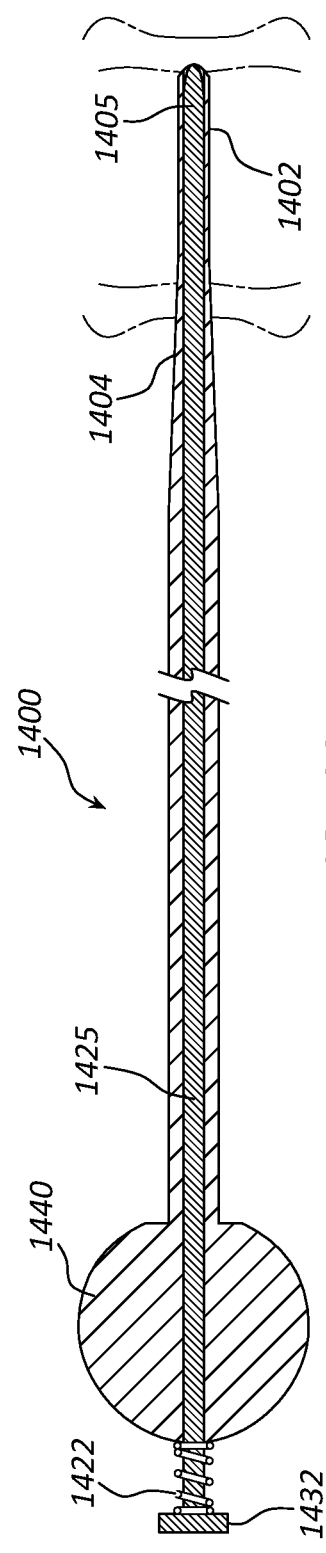
Figure 14C:
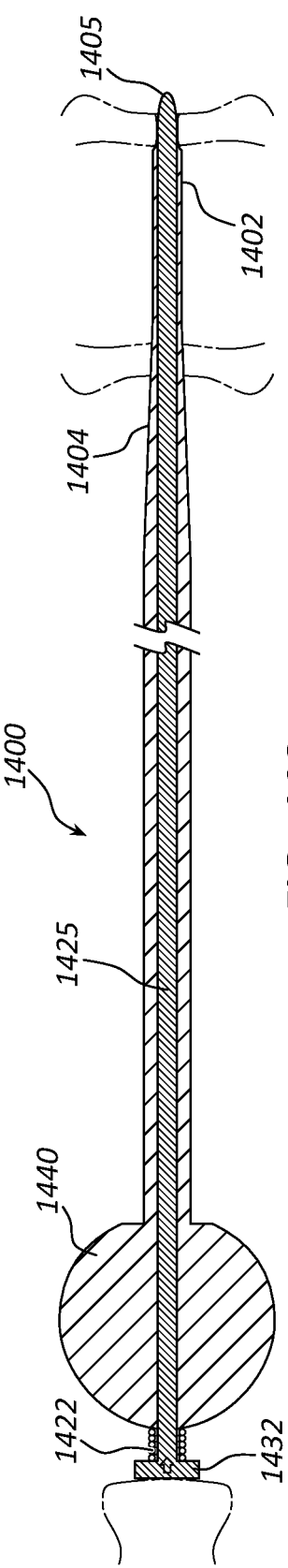

Another embodiment of a probe 1400 is shown in FIGS. 14A-14C, which is also shown in cross section during a probing procedure. As shown in these figures, probe 1400 may comprise one or more of the features previously mentioned, such as a shaft having a cylindrical portion 1402, a tapering portion 1404, and a tip 1405, which, again, may be similar in shape and function to those discussed above and therefore may have a shape that, in at least one dimension, is less than that of the adjacent probe body so as to create one or more ledges or shelves and/or may comprise flattened upper and/or lower surfaces so as to form a plate or plate-like shape.

Probe 1400 again comprises a spring-loaded tip 1405, but functions in a distinct manner vis-à-vis probe 1300. Like probe 1300, probe 1400 comprises an inner shaft or rod 1425 that is slidably positioned within an outer shaft portion and is rigidly coupled with tip 1405. However, rod 1425 extends proximally of handle 1440 and spring 1422 is positioned between handle 1440 and a proximal flange 1432 to form a plunger. Thus, tip 1405 is biased towards its retracted configuration rather than its extended configuration as with probe 1300. Again, another biasing member or other biasing means may be used in other contemplated embodiments.

Thus, as tip 1405 is advanced through a vertebral body 50 or other bone, as shown in FIGS. 14A and 14B, which may be done using handle 1440 but without contacting flange 1432 of the corresponding plunger mechanism, tip 1405 remains in contact with the adjacent portion of the outer shaft. Once tip 1405 contacts the distal cortical wall, as shown in FIG. 14B, the surgeon or other user may then tap the flange 1432 of the plunger mechanism to breach the distal cortical wall, as shown in FIG. 14C. A user may determine the position of the tip 1405 at the distal cortical wall by tactile feel, by way of a suitable sensor, or by any of the other means disclosed herein or otherwise available to those of ordinary skill in the art.

The distance with which tip 1405 extends through the distal cortical wall may be predetermined by way of the distance of the portion of shaft 1425 that extends proximally of the proximal wall of handle 1440. Again, this may ensure that the tip 1405 is only advanced by a desired amount and no more.

In some embodiments, tip 1405 may be recessed within the adjacent shaft, as shown in FIGS. 14A and 14B, until such time as tip 1405 is advanced by depressing the aforementioned plunger mechanism. In this manner, the adjacent portion of the shaft may contact the distal cortical wall, in some embodiments simultaneously with the distal end of the tip 1405, which may provide additional protection against undue advancement of the probe 1400. Alternatively, tip 1405 may protrude from the lumen defined by the shaft before depressing the plunger mechanism.

Figure 15A:
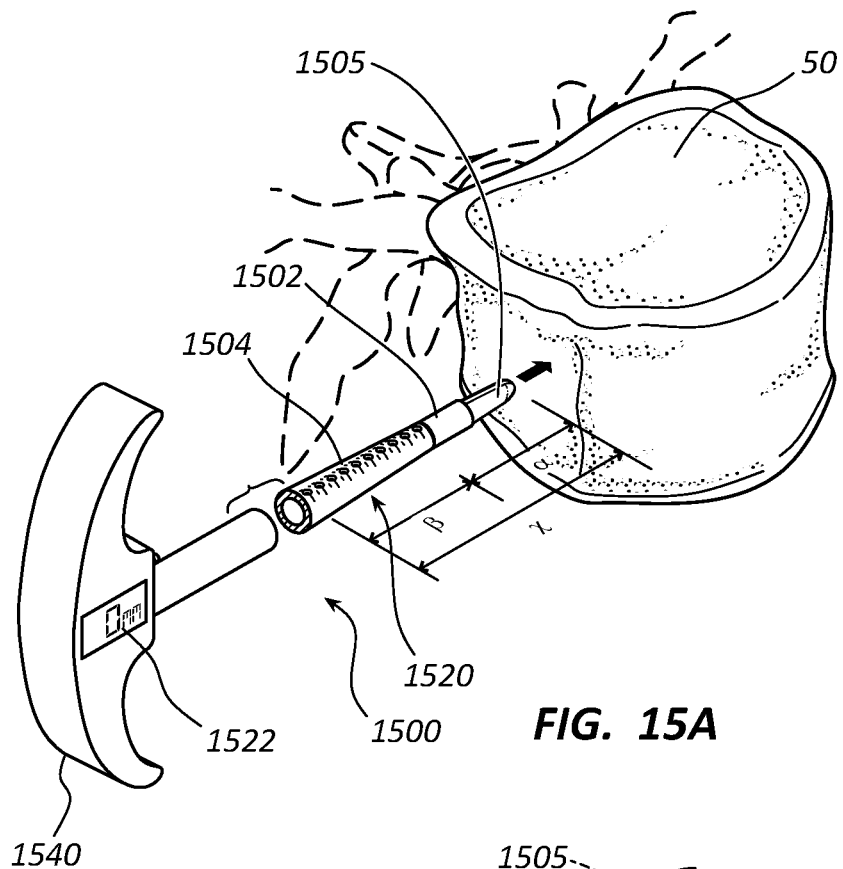
FIGS. 15A and 15B are perspective views of a vertebral probe being used to probe a vertebral body according to further embodiments.
Figure 15B:
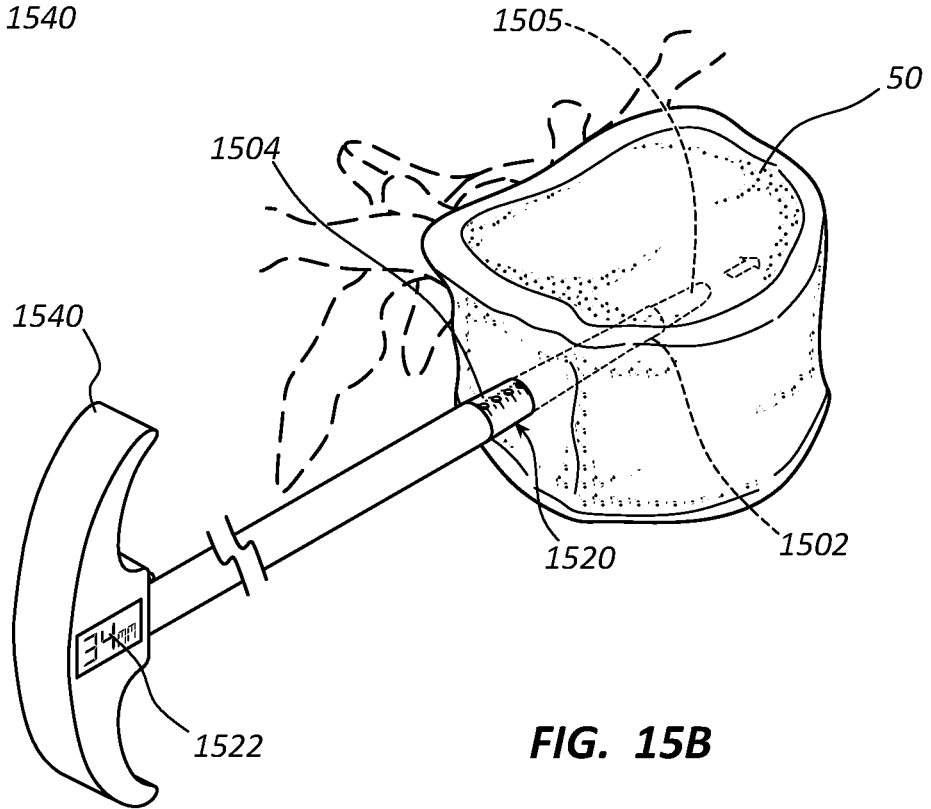

Yet another embodiment of a probe 1500 is shown in FIGS. 15A and 15B, which are perspective view of probe 1500 during a probing procedure, again, involving a vertebral body 50. As shown in these figures, probe 1500 may comprise one or more of the features previously mentioned, such as a shaft having a cylindrical portion 1502, a tapering portion 1504, and a tip 1505, which, again, may be similar in shape and function to those discussed above and therefore may have a shape that, in at least one dimension, is less than that of the adjacent probe body so as to create one or more ledges or shelves and/or may comprise flattened upper and/or lower surfaces so as to form a plate or plate-like shape.

Probe 1500 comprises another alternative, automated means for identifying a current location of the tip 1505 or another portion of probe 1500 within a vertebral body or other bony structure. In particular, probe 1500 comprises an array 1520 of sensors and/or lights that may be used to provide a signal to display 1522 to provide an automated, electronic indication of the depth of probe 1500 during a probing procedure. In some embodiments, array 1520 may comprise a series of lasers and/or openings in the shaft of probe 1500 to allow for such lasers, or other lights, such as LEDS, to extend therethrough. As the shaft of probe 1500 is advanced, each element of array 1520 extends through the proximal cortical wall of vertebral body 50, as shown in FIG. 15B. As the light and/or sensor from each element of array 1520 contacts the adjacent bone of the cortical wall, a signal may be sent to update the display 1522 and provide a depth indication. In some embodiments, additional alarms, such as audible and/or visual alarms, may be provided to indicate, for example that the tip 1505 is at or near the distal cortical wall.

Figure 16A:
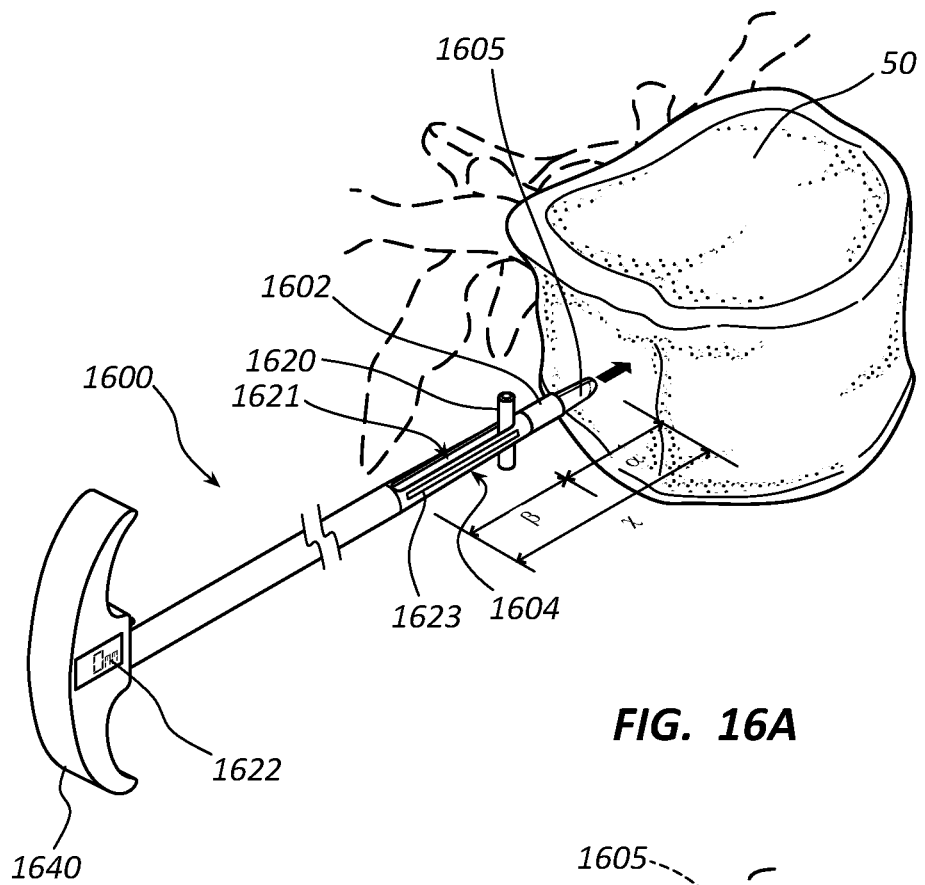
FIGS. 16A and 16B are perspective views of another vertebral probe being used to probe a vertebral body.
Figure 16B:
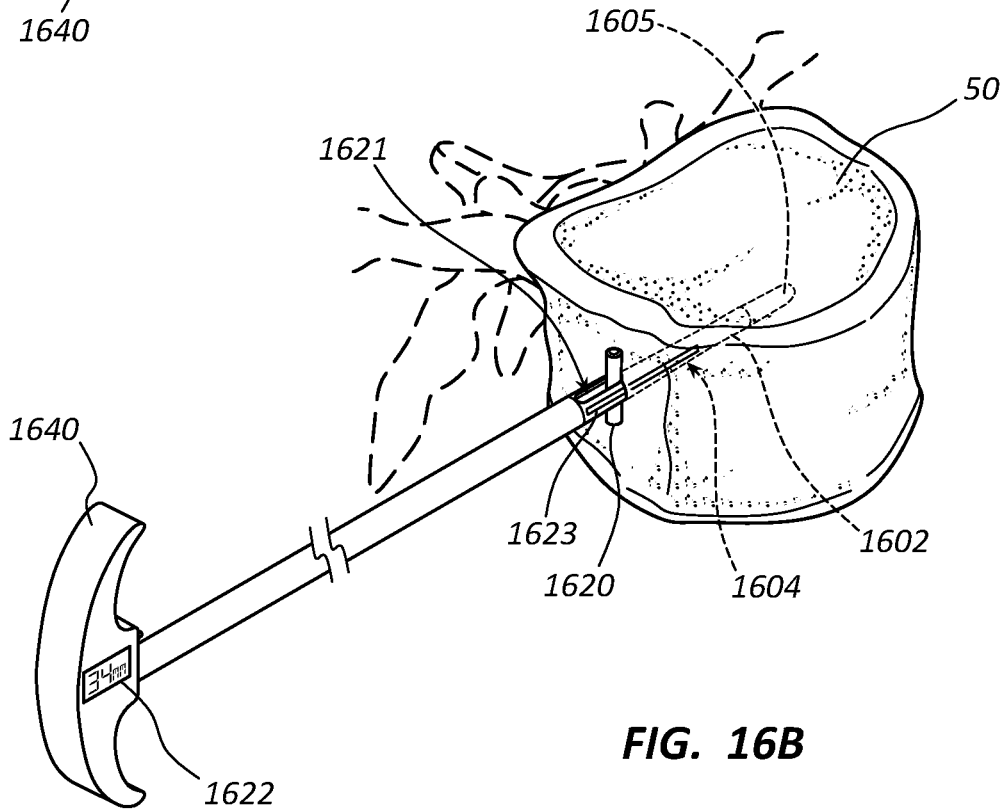

An embodiment of a vertebral probe 1600 combining features from previous embodiments is shown in FIGS. 16A and 16B. It should be understood however, that any of the features, elements, etc. of any of the disclosed embodiments may be combined with other features, elements, etc. as desired. Similar to probe 1000, probe 1600 further comprises an automated means for identifying a current location of the tip 1605 or another portion of probe 1600 within a vertebral body or other bony structure. However, the means provided for in this embodiment combines the mechanical means of probe 1000 with a sensor or other electronic means to provide a readout to display 1622, which may be on handle 1640.

Thus, like probe 1000, probe 1600 comprises a bone engaging member 1620, configured to engage a proximal cortical wall of a vertebral body 50 and, as tip 1605 passes through the inner/cancellous portion of the vertebral body, maintains contact with this cortical wall but is movably engaged with at least a portion of the shaft. In this embodiment, however, one or more sensors 1623 may be provided to provide an electronic indication of the position of bone engaging member/pin 1620, which is slidably positioned within a slot or window 1621 formed in a portion of the shaft of probe 1600. By sensing the position of bone engaging member/pin 1620 vis-à-vis the adjacent shaft portion as it moves relative to the outer portion of the shaft, the position of bone engaging member/pin 1620 may be determined, which may provide an indication of the depth with which tip 1605 has penetrated into vertebral body 50. After proper calibration, as those of ordinary skill in the art will appreciate and understand, a depth indication may then be provided by a signal received from sensor 1623 on display 1622. Display 1622 may provide, for example, a number indicating the current depth of the tip 1605 or another part of probe 1600 or may provide other suitable indicia of such depth, such as lights that change depending upon the current depth, audible alerts when tip 1605 is at or near the distal cortical wall of vertebral body 50, or the like.

As previously described in connection with other embodiments, a spring or other biasing member (not visible in FIGS. 16A and 16B) may be provided to allow bone engaging member 1620 to preferably be biased towards a distal direction relative to other portions of the probe 1600, such as the tip 1605, such that bone engaging member 1620 maintains contact with, for example, the proximal cortical wall of a vertebral body 50 while the tip 1605 is advanced through the vertebral body 50.

Figure 17A:
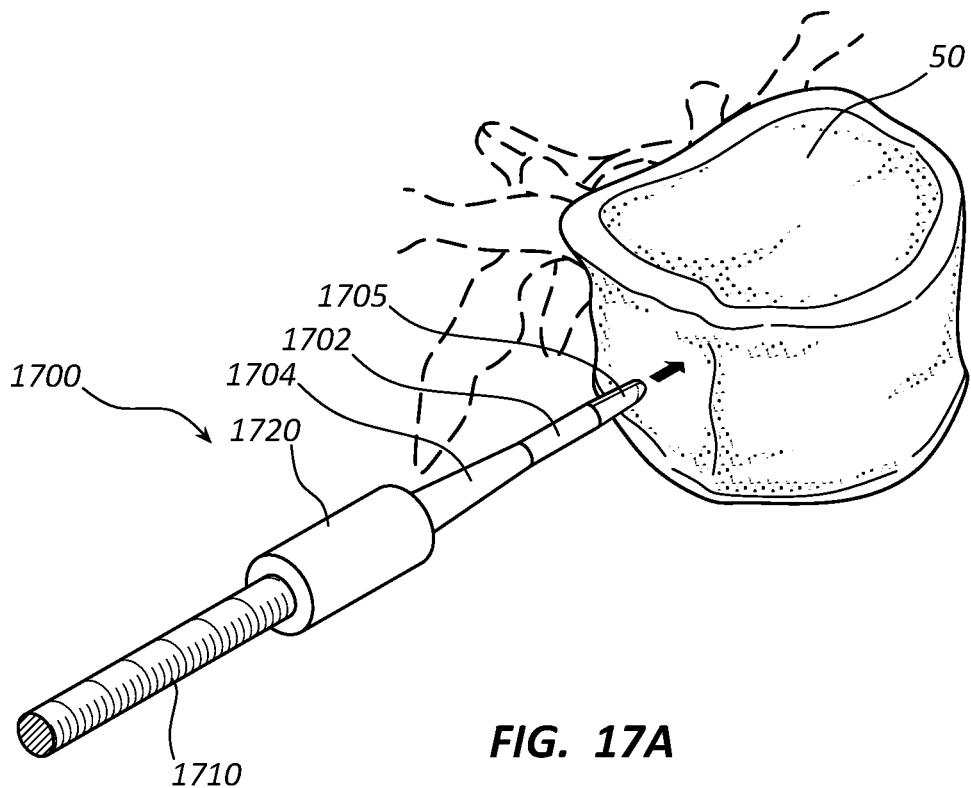
FIGS. 17A and 17B are perspective views of yet another vertebral probe being used to probe a vertebral body.
Figure 17B:
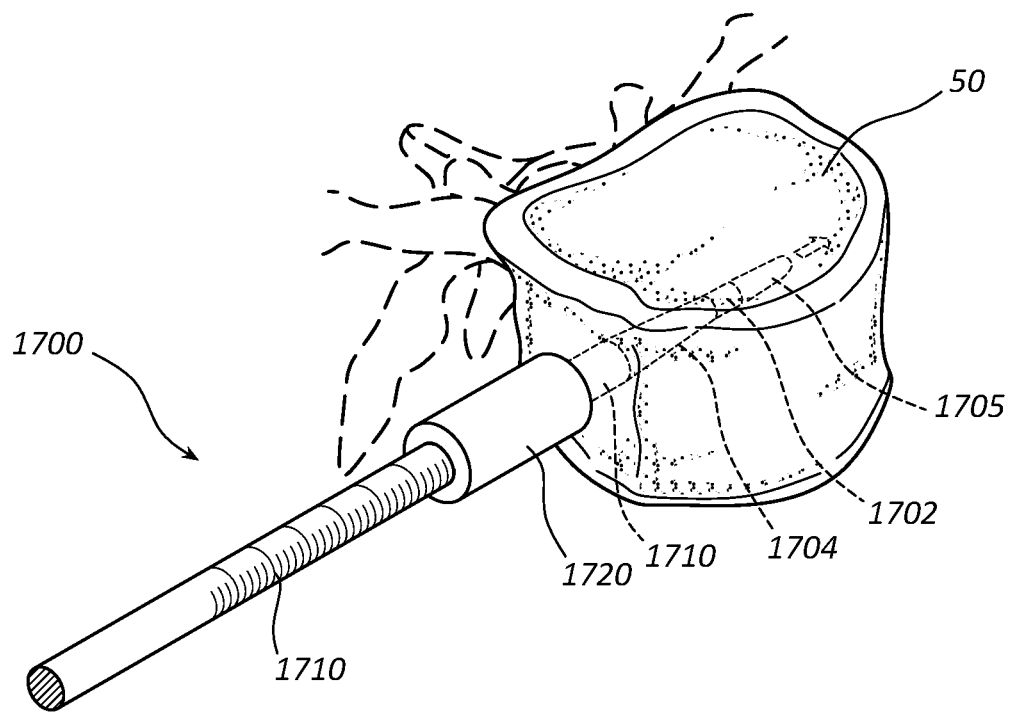

Another example of a bone probe 1700 is shown in FIGS. 17A and 17B, which is configured for probing bone of varying density, particularly a vertebral body 50, as previously described. Bone probe 1700 again comprise a tip 1705 that preferably comprises a shape and/or features that allow for a tactile feel when tip 1705 penetrates through a cortical wall of vertebral body 50 and/or provides for an increase in force following such penetration to a predetermined distance, such as by providing a ledge and/or shelf, as described throughout this disclosure. Bone probe 1700 may also comprise a tapering section 1704 and may further comprise one or more non-tapering and/or cylindrical sections 1702.

Probe 1700 further comprises yet another example of an automated means for identifying a current location of the tip 1705 or another portion of probe 1700 within a vertebral body 50 or other bony structure during a probing procedure. In particular, probe 1700 comprises a collar 1720 slidably positioned on the shaft that may be used to identify a location of the tip 1705 or another portion of the probe 1700 after tip 1705 penetrates the proximal cortical wall of vertebral body 50, as shown in FIG. 17B. By providing a series of tick marks, alphanumeric characters, or other markings 1710 on the shaft, as the probe passes through vertebral body 50, collar 1720 contacts the proximal cortical wall and slides along the shaft of probe 1700 adjacent to markings 1710. As previously described, this may allow a surgeon or other user to identify a location, or an at least approximate location, of the tip 1705 within the vertebral body 50.

In some embodiments, markings 1710 may be broken up into sections that may correspond with various regions within the vertebral body 50. For example, a green section may be used to indicate passage through a central, cancellous region of the bone and a yellow section may indicate that the tip 1705 is close to the distal cortical wall, and a red region may be used to indicate that the tip 1705 is at or very near the distal cortical wall to allow a surgeon to adjust the probing force used accordingly. Again, other notification and/or electronic means, such as sensors, speakers, LEDs, and the like, may be used as well to provide warnings at particular locations if desired.

Although collar 1720 is shown as being somewhat elongated, it is also contemplated that shorter collars, such as rings, may be used in alternative embodiments. In addition, in order to keep the collar 1720 in place on the shaft of probe 1700, a friction fit may be used or, alternatively, a series of indentations and/or teeth may be used to allow collar 1720 to move in a step-wise fashion along the shaft of probe 1700. In some embodiments, the shaft may also, or alternatively, comprise a similar series of indentations and/or teeth to allow for advancement in a manner similar to a ratchet mechanism.

Figure 18A:
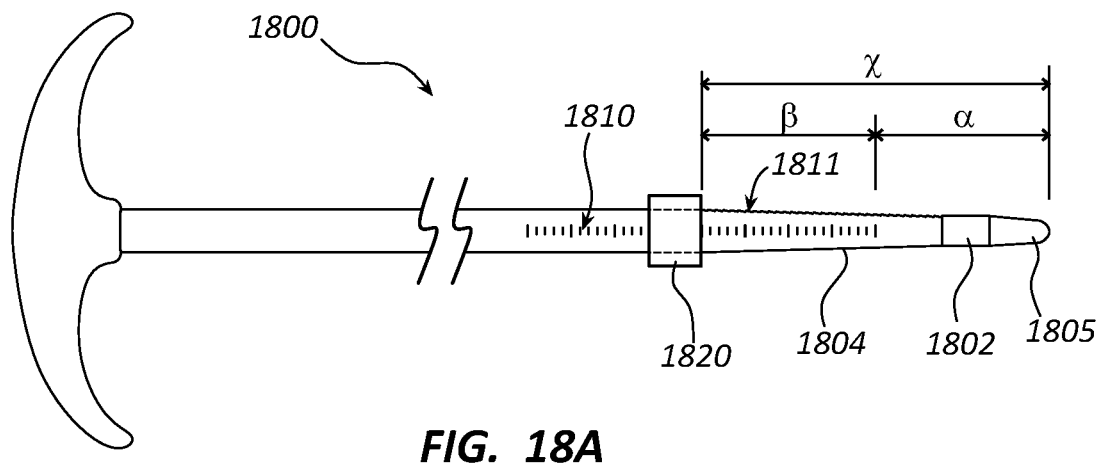
FIGS. 18A and 18B depict another vertebral probe comprising a slidable ring in two stages of use with the ring moving relative to the adjacent portion of the probe shaft.
Figure 18B:
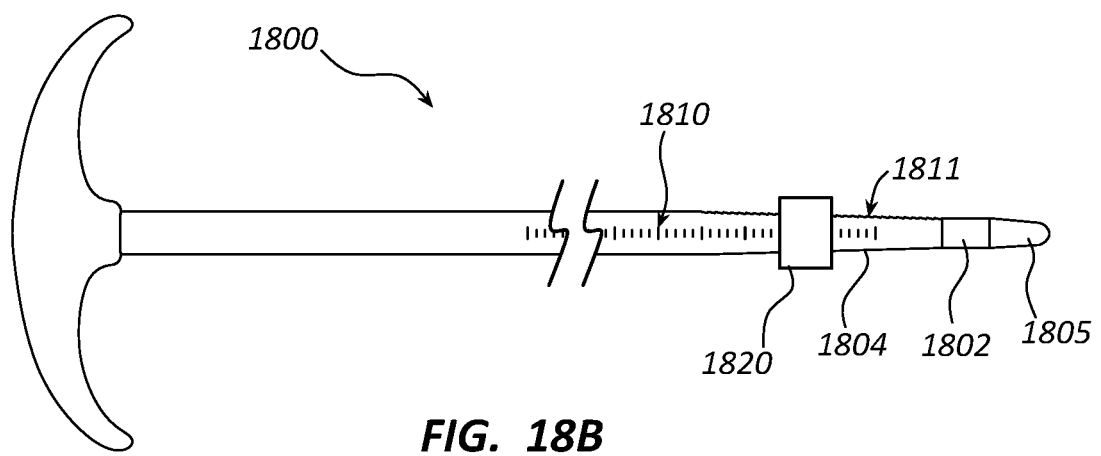

A more specific embodiment of a vertebral probe 1800 including these features is depicted in FIGS. 18A and 18B. In particular, probe 1800 comprises a tapering section 1804 and tip 1805 as previously described, along with a ring 1820 that is slidably positioned along the shaft of the probe 1800. In a manner similar to that described above, ring 1820 may contact a vertebral body or other outer surface of a bone (not shown in these figures), which may force ring 1820 to slide along the shaft relative to tip 1805 and/or the remainder of probe 1800, as shown in FIG. 18B. A series of markings 1810 may be provided to allow a surgeon or other user to gauge the depth of probe 1800 at any given moment during a probing procedure.

Ring 1820 may slide along the shaft of probe 1800 smoothly and therefore be configured for being positioned at an infinite number of positions thereon. However, in other embodiments, a plurality of teeth, protrusions, and/or indentations may be provided such that ring 1820 is advanceable to only a series of predetermined positions dictated by these structures. In some embodiments, such teeth, protrusions, and/or indentations may be used as the markings 1810, if sufficiently visible. Alternatively, markings 1810 may be provided adjacent to the teeth 1811, protrusions, and/or indentations, if present.

Figure 19:
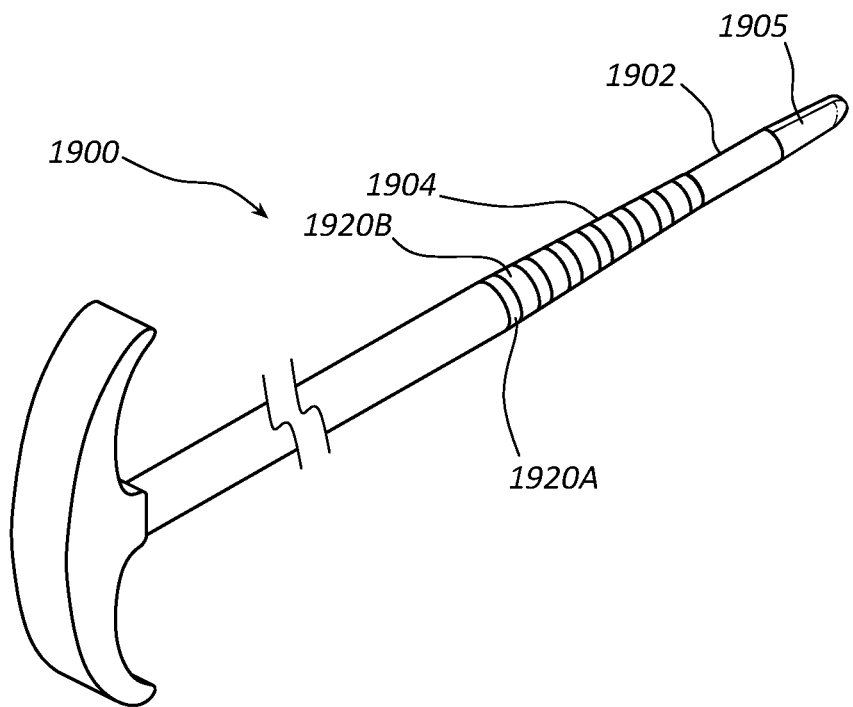
FIG. 19 is a perspective view of a vertebral probe having a section with radiographic markers of varying radiopacity.

FIG. 19 illustrates another example of a vertebral probe 1900 configured with still other possible features to facilitate determining a current location of the probe 1900 within a vertebral body or other bony structure during a probing procedure. In this depicted embodiment, a probing portion (portion configured to enter the vertebral body or other bone) of probe 1900 comprises one or more radiographic markers 1920 that is configured to allow a surgeon or other user to identify the probing depth with greater precision than simply providing a probe that is radiopaque.

In the depicted embodiment, radiographic marker section 1920 comprises a plurality of adjacent sections that vary in terms of their radiopacity. More particularly, section 1920 comprises a plurality of radiolucent sections 1920A and a plurality of radiopaque sections 1920B. In should be understood that sections 1920A and 1920B need not be fully radiopaque or fully radiolucent but the radiolucent sections 1920A should at least be more radiolucent that radiopaque sections 1920B, and vice versa, to allow for a surgeon or other user to be able to visually distinguish them while viewed during radiography.

Preferably, section 1920 is specifically positioned along the shaft of probe 1900 at a location that corresponds with known depths associated with probing a specific vertebral body or other bone. For example, section 1920 may begin adjacent to tip 1905 and may end at a position at or near where the proximal end of the probe 1900 is expected to be following breach of the distal cortical wall. Tip 1905 may be adjacent to non-tapering section 1902, which may be adjacent to tapering section 1904, which may coincide and/or overlap with section 1920.

The spacing of the adjacent sections of section 1920 may also be configured to have specific distances therebetween to allow a surgeon to gauge distances as the probe 1900 is advanced. For example, in some embodiments, each radiolucent section 1920A may be spaced apart from one or more adjacent radiolucent sections by between about 5 to about 10 mm. In some embodiments, a probe 1900 comprises one or more radiolucent markers may be manufactured by providing a relatively thin metallic or other radiopaque core having plastic or other radiolucent material bands positioned thereon at spaced intervals. The radiolucent sections may therefore have a central or other portion that is radiopaque. The radiopaque sections may be formed from the same radiopaque material as the core or a different material if desired.

A wide variety of alternative embodiments are also contemplated. For example, section 1920 may comprise only a single marker having a different radiopacity than the rest of probe 1900 or may comprise only two such markers spaced at an appropriate interval to match or at least substantially correspond with the expected length/width of the vertebral body. For example, a marker may be positioned at a point where, once the marker is at or near the proximal cortical wall, the surgeon may be able to determine that the tip 1905 is at or near the distal cortical wall by seeing the marker.

Figure 20A:
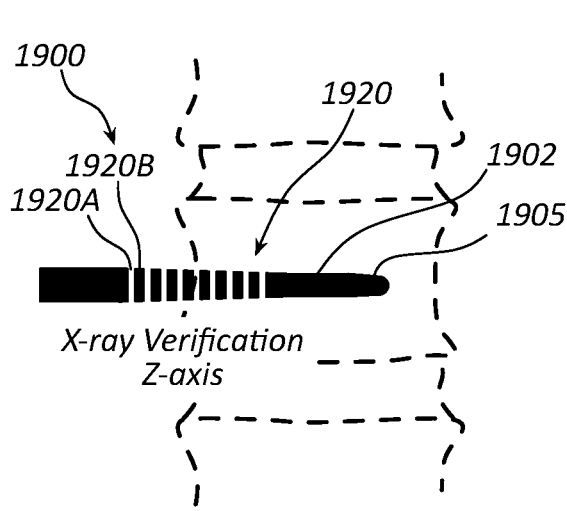
FIGS. 20A-20C depict the vertebral probe of FIG. 19 under various radiographic views during a probing procedure.
Figure 20B:
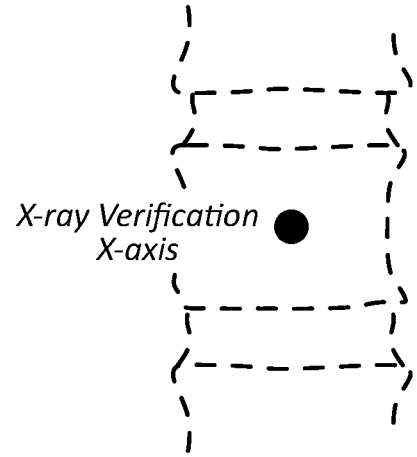
Figure 20C:
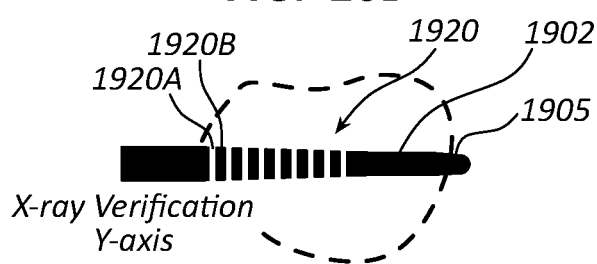

FIGS. 20A-20C illustrate several views of probe 1900 including sections 1920A and 1920B, under radiography. As shown in these views, providing markers that are visually distinguishable from one another, preferably by virtue of using materials having differing radiopacity, a user can better visualize the location of the probe 1900 and thereby enhance the safety of the procedure and/or the proper path of the probe 1900 during the procedure.

In some embodiments, the handle and/or the entire portion of the shaft/probe 1900 proximal of the portion that is expected to enter a vertebral body, which may coincide with the start of section 1920 on the proximal side, may be formed from a radiolucent material. This may allow for better visualization of the probing portion of the probe 1900 during a procedure by avoiding the other parts from obscuring the view of the probing portions, such as section 1920.

FIG. 21 illustrates another vertebral probe 2100 according to other embodiments. Probe 2100 again comprises a shaft having a tapering portion 2104 and a tip 2105. Other portions, such as a non-tapering portion 2102 adjacent to tapering portion 2104 on one or both sides of tapering portion 2104 may be provided if desired. Tip 2105 may be similar in shape and function to those discussed above and therefore may have a shape that, in at least one dimension, is less than that of the adjacent probe body so as to create one or more ledges or shelves and/or may comprise flattened upper and/or lower surfaces so as to form a plate or plate-like shape. Probe 2105 may further comprise various other elements previously described, such as bone density and/or pressure sensor 2120 that may be configured to sense one or more variables to allow for automated and/or electronic confirmation of the current position of the probe 2100 within vertebral body 50.

Probe 2100 may further comprise any of the previously described means for notifying a surgeon or practitioner as to the density of the bone at the tip 2105 and/or as to the position of the tip 2105 or another portion of probe 2100 within vertebral body 50 or another bone, such as display 2122, which may comprise, for example, one or more LEDs or other lights, speaker 2124, or the like. In some embodiments and implementations, probe 2100 may therefore be configured to provide a visual and/or audible alert when tip 805 of probe 800 is at or near a cortical bone region, such as when tip 2105 is at or near the distal cortical wall of vertebral body 50. A switch, button, or other actuation means 2126 may also be provided to actuate one or more of the electronic elements of probe 2100.

However, unlike the probes previously described, probe 2100 further comprises an angled shaft, which may, for example, extend the proximal portion of the shaft from the distal portion of the shaft at an angle of, for example, between about 5 and about 15 degrees. This angulation may be particularly useful in connection with probing specific regions of a patient's spine, such as the T4-6 region of the spine. In some embodiments, the shaft may be configured to allow for adjustment of the angle. For example, the shaft may be made up of a flexible material configured to bend at a desired angle and/or be provided with a mechanism for bending and/or locking the shaft, such as the mechanism disclosed in U.S. Patent Application Publication No. 2010/0249497 titled Surgical Instrument, the disclosure of which is incorporated herein by reference in its entirety. Preferably, the point along the shaft at which the curvature/angulation starts may be between about 25 and about 50 mm from the distal end of tip 2120.

FIG. 21 also illustrates the possible use of various x-ray images that may be taken along mutually perpendicular axes, such as the indicated x, y, and z axes. FIGS. 22A-22C illustrate possible views of the probe 2100 that may be used to verify the position thereof during a probing procedure.

Examples of means for visually and/or audibly notifying a surgeon or practitioner as a current position of a probe tip or another portion of a probe within a vertebral body or other bone having varying bone densities, which may replace or complement the means for providing a tactile notification of a transition between such varying bone densities provided by the various tips disclosed herein, include sensors 820, 1520, 1623, and 2120, along with their respective, related functional components, bone engaging member 1020, along with its related functional components, and collar 1720 and ring 1820, along with their respective, related functional components.

Examples of means for advancing a probe tip through a cortical wall or other bony structure by only a predetermined amount, which may also replace or complement the means for providing a tactile notification of a transition between such varying bone densities provided by the various tips disclosed herein, include bone engaging member 1620 along with its related functional components and the spring-loaded tip of probe 1300 and its related functional components.

It will be understood by those having skill in the art that changes may be made to the details of the above-described embodiments without departing from the underlying principles presented herein. Any suitable combination of various embodiments, or the features thereof, is contemplated.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Throughout this specification, any reference to "one embodiment," "an embodiment," or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure.

This method of disclosure, however, is not to be interpreted as reflecting an intention that any claim require more features than those expressly recited in that claim. Rather, inventive aspects lie in a combination of fewer than all features of any single foregoing disclosed embodiment. It will be apparent to those having skill in the art that changes may be made to the details of the above-described embodiments without departing from the underlying principles set forth herein.

Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. The scope of the present invention should, therefore, be determined only by the following claims.

The invention claimed is:

1. A vertebral probe for use in spinal surgeries, comprising:
    a shaft; and
    a tip positioned at a distal end of the shaft and configured to penetrate a vertebral body to facilitate subsequent placement of a bone anchor providing bicortical purchase within the vertebral body, wherein the tip is axially movable relative to the shaft during a spinal surgery, wherein the tip comprises a non-circular shape in cross-section, at least in part, wherein the tip extends from a shelf that faces distally towards the tip, wherein the shelf defines an engaging surface configured to engage an outer surface of cortical wall of the vertebral body during a spinal surgery after the tip has penetrated the cortical wall to increase an insertion force needed for continued advancement of the vertebral probe through the vertebral body following engagement of the outer surface of the cortical wall by the shelf, and wherein the tip is axially movable relative to the shelf.

2. The vertebral probe of claim 1, wherein at least a portion of the vertebral probe is spring-loaded.

3. The vertebral probe of claim 2, wherein the tip comprises a spring-loaded tip.

4. The vertebral probe of claim 3, wherein the tip is biased away from the shaft, wherein the tip is configured to retract relative to the shaft while the tip is advanced through cancellous bone in a vertebral body, and wherein the tip is configured to automatically axially protrude relative to the shaft upon breach of a distal cortical wall in the vertebral body.

5. The vertebral probe of claim 4, further comprising a sensor configured to detect a breach of the distal cortical wall during use.

6. The vertebral probe of claim 5, further comprising a notification means for notifying a user when a breach of the distal cortical wall has occurred, wherein the sensor is communicatively coupled with the notification means.

7. The vertebral probe of claim 1, wherein the tip is defined, at least in part, by opposing flat surfaces extending from the shaft.

8. The vertebral probe of claim 1, wherein the vertebral probe is configured to allow for penetration of the tip through a cortical wall of a vertebral body with a first force and further configured to inhibit further advancement of the vertebral probe by requiring a second force substantially greater than the first force to achieve further advancement of the vertebral probe within the vertebral body, and wherein the tip comprises a blunt tip.

9. The vertebral probe of claim 1, wherein the distal end of the tip is devoid of any sharp points or edges.

10. The vertebral probe of claim 1, wherein the tip is defined, at least in part, by opposing flat surfaces extending from the shaft, and wherein the opposing flat surfaces are at least substantially parallel to one another.

11. The vertebral probe of claim 1, further comprising a handle at a proximal end of the shaft configured to allow a surgeon to operate the vertebral probe.

12. The vertebral probe of claim 1, wherein the shelf is configured to allow the tip to penetrate through a proximal cortical wall with a first force and subsequently allow the shelf to engage the proximal cortical wall to inhibit further advancement of the vertebral probe by requiring a second force substantially greater than the first force to achieve further advancement of the vertebral probe.

13. The vertebral probe of claim 1, further comprising a sensor configured to detect a breach of the distal cortical wall during use.

14. The vertebral probe of claim 13, wherein the tip comprises a spring-loaded tip, and wherein the sensor is configured to detect a state of contraction associated with the spring-loaded tip.

15. The vertebral probe of claim 14, wherein the sensor is configured to detect breach of the distal cortical wall by detecting spikes in movement of the spring-loaded tip.

16. The vertebral probe of claim 13, further comprising notification means for notifying a user when a breach of the distal cortical wall has occurred, wherein the sensor is communicatively coupled with the notification means.

17. The vertebral probe of claim 13, further comprising an output coupled with the sensor, wherein the output is configured to notify a user when a breach of the distal cortical wall is detected.

18. A vertebral probe for use in spinal surgeries, comprising:
    a handle;
    a shaft; and
    a tip positioned at a distal end of the shaft and configured to penetrate a vertebral body to facilitate subsequent placement of a bone anchor providing bicortical purchase within the vertebral body, wherein the tip is axially movable relative to the shaft, wherein the tip comprises a non-circular shape in cross-section, at least in part, wherein the tip is biased away from the shaft, wherein the distal end of the tip is devoid of any sharp points or edges, and wherein the tip is axially movable relative to an immediately adjacent engaging portion of the shaft configured to engage a cortical wall of the vertebral body.

19. The vertebral probe of claim 18, wherein the engaging portion comprises a shelf.

* * * * *